(12) United States Patent
Walker et al.

(10) Patent No.: US 12,224,041 B2
(45) Date of Patent: Feb. 11, 2025

(54) ASSAY FOR HEMOGLOBIN A (HBA) DETECTION AND GENOTYPING

(71) Applicant: Laboratory Corporation of America Holdings, Burlington, NC (US)

(72) Inventors: Andrew Walker, Somerville, MA (US); Matt Robinson, Raleigh, NC (US)

(73) Assignee: Laboratory Corporation of America Holdings, Burlington, NC (US)

( * ) Notice: Subject to any disclaimer, the term of this patent is extended or adjusted under 35 U.S.C. 154(b) by 440 days.

(21) Appl. No.: 17/193,629

(22) Filed: Mar. 5, 2021

(65) Prior Publication Data

US 2021/0280269 A1 Sep. 9, 2021

Related U.S. Application Data

(60) Provisional application No. 62/986,152, filed on Mar. 6, 2020.

(51) Int. Cl.
*G16B 20/10* (2019.01)
*G01N 27/447* (2006.01)
*G16B 40/00* (2019.01)

(52) U.S. Cl.
CPC ....... *G16B 20/10* (2019.02); *G01N 27/44782* (2013.01); *G16B 40/00* (2019.02)

(58) Field of Classification Search
CPC ........ G16B 20/10; G16B 40/00; G16B 20/20; G01N 27/44782; Y02A 50/30; C12Q 1/6883; C12Q 2600/156
See application file for complete search history.

(56) References Cited

PUBLICATIONS

Rajan-Babu I-S, Chong SS. Molecular Correlates and Recent Advancements in the Diagnosis and Screening of FMR1-Related Disorders. Genes. 2016; 7(10):87. https://doi.org/10.3390/genes7100087 (Year: 2016).*
Hunter, J. E., Berry-Kravis, E., Hipp, H., & Todd, P. K. (2019). FMR1 disorders. (Year: 2019).*
A. H. Shurrab and A. Y. A. Maghari, "Blood diseases detection using data mining techniques," 2017 8th International Conference on Information Technology (ICIT), Amman, Jordan, 2017, pp. 625-631, doi: 10.1109/ICITECH.2017.8079917. (Year: 2017).*
Liu, J. Z., Han, H., Schouten, J. P., Wang, L. R., Fan, X. P., Duarte, H. B., . . . & Wang, Q. T. (2008). Detection of α-thalassemia in China by using multiplex ligation-dependent probe amplification. Hemoglobin, 32(6), 561-571. (Year: 2008).*
Coffa J. (2013). Coffalyser.NET analysis manualbetaversion. Version 0.1.https://manualzz.com/doc/6931311/coffalyser.net-analysis-manual (Year: 2013).*
Blattner, A. et al., "Detection of germline rearrangements in patients with α- and β-thalassemia using high resolution array CGH," Blood Cells, Molecules and Diseases 51:39-47 (2013).
Camaschella, C. et al., "Different Hematological Phenotypes Caused by the Interaction of Triplicated α-Globin Genes and Heterozygous β-Thalassemia," Am. J. Hematol. 55:83-88 (1997).
Coelho, A. et al., "Novel large deletions in the human α-globin gene cluster: Clarifying the HS-40 long-range regulatory role in the native chromosome environment," Blood Cells, Molecules, and Diseases, doi:10.1016/j.bcmd.2010.05.010.
Colosimo, A. et al., "Application of MLPA assay to characterize unsolved α-globin gene rearrangements", Blood Cells, Molecules & Diseases, 46(2):139-144 (2010).
Dillman, A., "MLPA Analysis Using GeneMarker Software", Available online at: https://softgenetics.com/PDF/MLPA_2014_AppNote.pdf, 2014, pp. 1-3.
Gilad, O. et al., "Characterization of Two Unique α-Globin Gene Cluster Deletions Causing α-Thalassemia in Israeli Arabs," Hemoglobin 38(5):319-324 (2014).
Goossens, M. et al., "Triplicated α-globin loci in humans," Proc. Natl. Acad. Sci. USA 77(1):518-512 (1980).
Grosso, M. et al., "Prenatal diagnosis of haemoglobinopathies: our experience of 523 cases," Clin. Chem. Lab. Med. 51(12):2219-2225 (2013).
Harteveld, C., "State of the art and new developments in molecular diagnostics for hemoglobinopathies in multiethnic societies," Int. J. Lab. Hem. 36:1-12 (2014).
Harteveld, C.L. et al., "Segmental duplications involving the α-globin gene cluster are causing β-thalassemia intermedia phenotypes in β-thalassemia heterozygous patients," Blood Cells, Molecules, and Diseases 40:312-316 (2008).
Harteveld, C. and Higgs, D., "α-thalassaemia," Harteveld and Higgs Orphanet Journal of Rare Diseases, 5(13) (2010), 21 pages.
Harteveld, C. et al., "Nine unknown rearrangements in 16p13.3 and 11p15.4 causing α- and β-thalassaemia characterised by high resolution multiplex ligation-dependent probe amplification," J. Med. Genet. 42(12):922-931 (2005).
Higgs, D.R. and Weatherall, D.J., "The Alpha Thalassaemias," Cell. Mol. Life Sci. 66:1154-1162 (2009).
Huang, J. et al., "A novel fusion gene and a common $\alpha^0$-thalassemia deletion cause hemoglobin H disease in a Chinese family," Blood Cells, Molecules and Diseases 51:31-34 (2013).

(Continued)

*Primary Examiner* — Kaitlyn L Minchella
*Assistant Examiner* — Nidhi Dharithreesan
(74) *Attorney, Agent, or Firm* — Kilpatrick Townsend & Stockton LLP

(57) ABSTRACT

Disclosed herein are techniques for implementation of a Hemoglobin A (HBA) assay and an HBA genotyping decision tree matrix in clinical testing. Particularly, aspects are directed to obtaining raw data from the HBA assay performed on a plurality of samples, calculating a first set of probe ratios for each sample based on the raw data, identifying a number of reference samples to be combined as a synthetic reference sample based on the first set of probe ratios, calculating a second set of probe ratios for each sample of the plurality of samples based on the raw data and the synthetic reference sample, and determining, by the decision tree matrix, an HBA genotype for each sample based on the second set of probe ratios for each sample and copy number calling thresholds for sample probe/reference probe ratios associated with each probe of the plurality of probes.

8 Claims, 8 Drawing Sheets

(56) References Cited

PUBLICATIONS

Hughes, J. et al., "Annotation of cis-regulatory elements by identification, subclassification, and functional assessment of multispecies conserved sequences," Proc. Natl. Acad. Sci. 102(28):9830-9835 (2005).

Jiang, H. et al., "Association of an α-Globin Gene Cluster Duplication and Heterozygous β-Thalassemia in a Patient with a Severe Thalassemia Syndrome," Hemoglobin 39(2):102-106 (2015).

Lin, M. et al., "Clinical and molecular characterization of a rare 2.4 kb deletion causing α+ thalassemia in a Chinese family," Blood Cells, Molecules, and Diseases 49:83-84 (2012).

Liu, J. et al., "Detection of α-Thalassemia in China by Using Multiplex Ligation-Dependent Probe Amplification," Hemoglobin 32(6):561-571 (2008).

Long, J. et al., "The diagnosis and molecular analysis of a novel 21.9kb deletion (Qinzhou type deletion) causing α+ thalassemia," Blood Cells, Molecules and Diseases 52:225-229 (2014).

Moosavi, S. et al., "The Carrier Frequency of α-Globin Gene Triplication in an Iranian Population with Normal or Borderline Hematological Parameters," Hemoglobin 35(4):323-330 (2011).

Nezhat, N. and Akbari, M., "Detection of Deletions/Duplications in α-Globin Gene Cluster by Multiplex Ligation-Dependent Probe Amplification," Genetic Testing and Molecular Biomarkers 16(7):684-688 (2012).

NCBI Accession No. NM-000558, Homo sapiens hemoglobin subunit alpha 1 (HBA1), mRNA (2018).

NCBI Accession No. NM-000517, *Homo sapiens* hemoglobin subunit alpha 2 (HBA2), mRNA (2018).

NCBI Accession No. NG-000006, *Homo sapiens* alpha globin region (HBA@); and hemoglobin subunit alpha 1 (HBA1); and hemoglobin subunit alpha (HBA2); and hemoglobin subunit mu (HBM); and hemoglobin subunit theta 1 (HBQ1); and hemoglobin subunit zeta (HBZ), RefSeqGene on chromosome 16 (2019).

Origa, R. et al., "Complexity of the alpha-globin genotypes identified with thalassemia screening in Sardinia," Blood Cells, Molecules and Diseases 52:46-49 (2014).

Phylipsen, M. et al., "A new α⁰-thalassemia deletion found in a Dutch family (-$^{AW}$)," Blood Cells, Molecules, and Diseases 45:133-135 (2010).

Phylipsen, M. et al., "A novel α⁰-thalassemia deletion in a Greek pateitn with HbH disease and β-thalassemia train," European J. Haematol. 88:356-362 (2011).

Phylipsen, M. et al., "Fine-Tiling Array CGH to Improve Diagnostics for α- and β-Thalassemia Rearrangements," Hum. Mutat. 33:272-280 (2012).

Schouten, J. et al., "Relative quantification of 40 nucleic acid sequences by multiplex ligation-dependent prove amplification," Nuc. Acids Res. 30(12):357 (2002), 13 pages.

Schwartz, M. et al., "Deletion of Exon 16 of the Dystrophin Gene Is Not Associated With Disease," Hum. Mutat., Mutation in Brief #948 (2007), 7 pages.

Suemasu, C.N. et al., "Characterization of alpha thalassemic genotypes by multiplex ligation-dependent probe amplification in the Brazilian population," Braz. J. Med. Biol. Res. 44(1):16-22 (2011).

So, C. et al., "Novel Point Mutation of the α2-Globin Gene (HBA2) and a Rare 2.4 kb Deletion of the α1-Globin Gene (HBA1), Identified in Two Chinese Patients with Hb H Disease," Hemoglobin 38(3):213-215 (2014).

So, C. et al., "Beta thalassaemia intermedia due to silent alpha globin gene quadruplication in an infant," Pathology 46(6):57-572 (2014).

Sollaino, M. et al., "Association of α globin gene quadruplication and heterozygous β thalassemia in patients with thalassemia intermedia," Haematologica 94:1445-1448 (2009).

Varga, R. et al., "MLPA-based evidence for sequence gain: Pitfalls in confirmation and necessity for exclusion of false positives," Anal. Biochem. 421:799-801 (2012).

Viprakasit, V. et al., "A novel deletion causing a thalassemia clarifies the importance of the major human alpha globin regulatory element," Blood 107(9):3811-3812 (2006).

Wei, X. et al., "Molecular characterization of a novel 27.6-kb deletion causing α⁺ thalassemia in a Chinese family," Ann. Hematol. 90:17-22 (2011).

Zhang, H. et al., "The Control of Expression of the α-Globin Gene Cluster," Int. J. Hematol. 76:420-426 (2002).

PCT/US2021/021134, International Search Report and Written Opinion, Jun. 14, 2021, 11 pages.

CA Application No. 3174183, "Office Action", Aug. 28, 2023, 4 pages.

EP Application No. 21715371.7, "Office Action", Oct. 12, 2023, 4 pages.

International Application No. PCT/US2021/021134, "International Preliminary Report on Patentability", Sep. 15, 2022, 8 pages.

\* cited by examiner

300

1. Denaturation and Hybridization

2. Ligation

3. PCR with universal primers X and Y exponential amplification of ligated probes only

4. Fragment analysis

ASSAY FOR HEMOGLOBIN A (HBA) DETECTION AND GENOTYPING

CROSS-REFERENCE TO RELATED APPLICATIONS

This application claims the benefit of and priority to U.S. Provisional Application No. 62/986,152, filed on Mar. 6, 2020, which is hereby incorporated by reference in its entirety for all purposes.

FIELD

The present disclosure relates to Hemoglobin A (HBA) clinical testing, and in particular to techniques for a HBA assay and a HBA genotyping decision tree matrix for implementation into clinical testing.

BACKGROUND

Hemoglobin is an iron-rich protein in red blood cells that carries oxygen to cells throughout the body. The protein is composed of two α-globin and two β-globin subunits, the former coded for by the HBA1 and HBA2 genes, and the latter coded for by the HBB gene. When these genes are altered (changed) or missing, thalassemia occurs. The hemoglobin protein subunit affected in alpha thalassemia (α-thalassemia) is the alpha globin. People who inherit defective α-thalassemia gene that from one parent but and normal α-thalassemia genes from the other parent are carriers for α-thalassemia. Carriers of α-thalassemia usually have no signs or symptoms. However, they can pass the faulty genes on to their children. People who have moderate to severe forms of α-thalassemia have inherited multiple faulty α-thalassemia genes from both parents. These are inherited in an autosomal recessive pattern. α-Thalassemia is the most common inherited disorder of hemoglobin synthesis in the world, with mutant allele frequencies varying between 1% and 98% throughout the tropics and subtropics, where malaria is endemic. α-Thalassemia can occur in all ethnic groups but is more common in those of Southeast Asian descent. The high prevalence of α-thalassemia in specific populations is likely due to the protection from infection by the malaria parasite (multiple species of *Plasmodium*) that is offered by 1-2 defective copies of HBA genes. The American College of Obstetricians and Gynecologists recommends hemoglobinopathy screening for those of African, Southeast Asian, Mediterranean, Middle Eastern or West Indian descent, though hemoglobinopathies are becoming more prevalent in admixed populations.

Alpha globin coded for by two genes (α-globin genes, HBA1 and HBA2) on chromosome 16. Each person needs four functional HBA genes (two from each parent) to make enough α-globin for the body's hemoglobin to work normally. Different forms of α-thalassemia occur if one or more of these genes are defective. If one gene is defective, then a person is a "silent" carrier of the α-thalassemia trait and usually has no signs or symptoms. If two genes are defective, then a person has α-thalassemia trait (also called alpha thalassemia minor) and may have mild anemia. If three genes are defective, then a person has hemoglobin H disease. This can cause moderate to severe anemia. If all four genes are missing, then a person has α-thalassemia major (also called hemoglobin Bart's or hydrops fetalis). This is the most severe type of α-thalassemia. A fetus with this disorder will usually die in the womb or the baby will die soon after birth because the child is unable to make normal hemoglobin to carry oxygen throughout the body.

More than 90% of α-thalassemia results from the deletion of two or more copies of the α-globin genes (HBA1 and HBA2) on chromosome 16. The HBA1 and HBA2 genes are located within an ~30 kb α-globin gene cluster on chromosome 16, that includes the following alpha globin genes and (pseudogenes) from telomere to centromere in this order: HBZ, (HBZP1) .HBM, (HBAP1), HBA2, HBA1, HBQ1 (see, e.g., FIG. 1). The coding sequences of HBA1 and HBA2 are identical with divergent sequences located in the introns and 5'- and 3'-untranslated regions. In addition, the deletion of the HS-40 major hypersensitive site, which is located 40 kb upstream of the HBZ gene in the promoter region, affects RNA expression of both HBA1 and HBA2, thereby causing an α-thalassemia trait in heterozygotes. The Hb Constant Spring point mutation at the first base of the termination codon in HBA2 affects RNA expression of HBA2, and causing a more severe phenotype than a HBA2 deletion allele. Lastly, gene conversions are common between HBA1 and HBA2 due to their close proximity and high homology, but have no clinical significance. In view of these factors, it may be desirable to develop assays for HBA detection that are capable of genotyping multiple distinct loci of the α-globin region to easily screen for α-thalassemia.

SUMMARY

In various embodiments, a computer-implemented method is provided that includes: obtaining raw data from a Hemoglobin A (HBA) assay performed on a plurality of samples, wherein the HBA assay is performed using a plurality of probes capable of detection of copy number losses or gains in a α-globin gene cluster region of each sample of the plurality of samples, and the raw data comprises HBA copy number data for the plurality of probes resolved by capillary electrophoresis for each sample of the plurality of samples; selecting a reference sample from the plurality of samples; calculating a first set of probe ratios for each sample of the plurality of samples based on the raw data from the HBA assay and the reference sample; identifying a predetermined number of reference samples to be combined as a synthetic reference sample for the plurality of samples based on the first set of probe ratios; generating the synthetic reference sample based on the predetermined number of reference samples; calculating a second set of probe ratios for each sample of the plurality of samples based on the raw data from the HBA assay and the synthetic reference sample; iteratively inputting the second set of probe ratios for each sample into a decision tree matrix; determining, by the decision tree matrix, a HBA genotype for each sample based on the second set of probe ratios for each sample and copy number calling thresholds for sample probe/reference probe ratios associated with each probe of the plurality of probes; and providing the HBA genotype for each sample.

In some embodiments, wherein the calculating the first set of probe ratios comprises: (i) comparing control probe peak heights, or signals, in each sample of the plurality of samples to corresponding control probe peak heights, or signals, in the reference sample, (ii) calculating variability in signals between the control probe peak heights, or signals, in each sample and the corresponding control probe peak heights, or signals, in the reference sample as a control probe standard deviation, (iii) determining a sample of the plurality samples fails when any variability metrics are greater than a predetermined threshold, (iv) determining a sample of the plurality of samples does not fail when none of the variability metrics are greater than the predetermined threshold, and (v) for each sample that does not fail, comparing test probe peak heights, or signals, in the sample to corresponding test probe peak heights in the reference sample, and calculating a probe ratio between the test probe peak heights, or signals, in the sample and the corresponding test probe peak heights, or signals, in the reference sample.

In some embodiments, the calculating the second set of probe ratios comprises: (i) comparing the control probe peak heights, or signals, in each sample of the plurality of samples to corresponding control probe peak heights, or signals, in the synthetic reference sample, (ii) calculating variability in signals between the control probe peak heights, or signals, in each sample and the corresponding control probe peak heights, or signals in the synthetic reference sample as a control probe standard deviation, (iii) determining a sample of the plurality samples fails when any variability metrics are greater than the predetermined threshold, (iv) determining a sample of the plurality of samples does not fail when none of the variability metrics are greater than the predetermined threshold, and (v) for each sample that does not fail, comparing test probe peak heights, or signals, in the sample to corresponding test probe peak heights in the synthetic reference sample, and calculating a probe ratio between the test probe peak heights, or signals, in the sample and the corresponding test probe peak heights, or signals, in the synthetic reference sample.

In some embodiments, the determining the HBA genotype for each sample comprises: (i) determining aberrant probe ratio patterns for each sample based on the second set of probe ratios for each sample and the copy number calling thresholds for the sample probe/reference probe ratios associated with each probe of the plurality of probes, and (ii) identify the HBA genotype for each sample based on the aberrant probe ratio patterns.

In some embodiments, the determining the aberrant probe ratio patterns and the identifying the HBA genotype for each sample comprises: classifying each sample as normal, having a copy number variation (CNV), or as polymorphic based on the aberrant probe ratio patterns; and sub classifying any sample classified as having the CNV as a large targeted deletion, duplication or 'other' based on the aberrant probe ratio patterns.

In some embodiments, the determining the aberrant probe ratio patterns and the identifying the HBA genotype for each sample further comprises: sub classifying any sample classified as having the large targeted deletion as a large heterozygous deletion or a homozygous deletion; sub classifying any sample classified as the large heterozygous deletion or the homozygous deletion for one or more of the following deletions: SEA, FIL/THAI, MED or $\alpha^{20.5}$ based on the aberrant probe ratio patterns; and sub classifying any sample classified as having the large heterozygous deletion and one or more of the following: $\alpha^{3.7}$ deletion, $\alpha^{4.2}$ deletion, or $\alpha^{3.7}$ duplication based on the aberrant probe ratio patterns.

In some embodiments, the determining the aberrant probe ratio patterns and the identifying the HBA genotype for each sample further comprises: sub classifying any sample classified as having 'other'; sub classifying any sample classified 'other' as having $\alpha^{3.7}$ deletions, $\alpha^{4.2}$ deletions, and/or $\alpha^{3.7}$ duplications based on the aberrant probe ratio patterns.

In some embodiments, the method further comprises triggering performance of a confirmatory test on each sample of the plurality of samples that has the HBA genotype that is not normal or does not require manual review.

In some embodiments, a system is provided that includes one or more data processors and a non-transitory computer readable storage medium containing instructions which, when executed on the one or more data processors, cause the one or more data processors to perform part or all of one or more methods or processes disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present invention will be better understood in view of the following non-limiting figures, in which.

Figure 1:
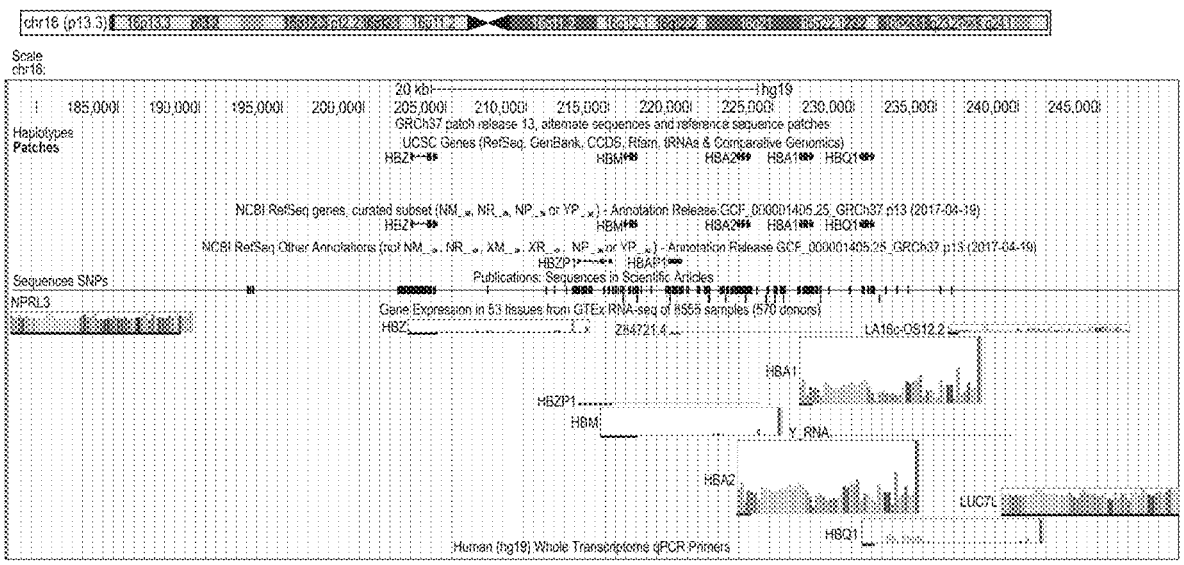
FIG. 1 shows gene data for chromosome 16 in accordance with various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. INTRODUCTION

DNA analysis of the α-globin region can be performed by targeting multiple distinct loci using multiplex ligation-dependent probe amplification (MLPA). This methodology, developed by MRC Holland (Product Description SALSA® MLPA® probemix P140-C1 HBA), detects genomic deletions and duplications involving this locus, including the seven most common types of α-thalassemia deletions ($\alpha^{3.7}$, $\alpha^{4.2}$, SEA, MED, THAI, FIL, and $\alpha^{20.5}$), as well the Constant Spring point mutation and the HBAx HS-40 promoter deletion. Conventionally the HBA MLPA copy number data is manually reviewed in order to determine genotype, due to the complexity of the α-globin region and number of loci analyzed by the MLPA assay. Confirmation testing may be performed by multiplex PCR and gel electrophoresis or Sanger sequencing. A problem associated with conventional HBA MLPA assays and manual genotyping is that they generate a large amount of MLPA copy number data from the α-globin region and utilize complex tables that guide the manual evaluation of the MLPA copy number data, which require extensive training experience and time. Moreover, conventional HBA MLPA assays typically demonstrate higher error rates for evaluation steps taken during manual genotyping. This error rate trickles down and undesirably impacts the quality of the screening test (e.g., false positives or over diagnosis) and may incorrectly trigger costly confirmation testing.

To address these limitations and problems, various embodiments described herein are directed to an HBA assay and genotyping technique capable of reducing ambiguity in decision-making and providing a comprehensive analysis of the consequences of each possible decision while achieving minimal error rate, with limited processing, memory and power resources. In some instances, processes were developed that include gating whether or not confirmation testing should be performed on a sample based on whether a decision tree concludes the samples includes a HBA genotype indicative of α-thalassemia. For example, various embodiments of the present disclosure include a system including one or more processors and a memory coupled to the one or more processors. The memory is encoded with a set of instructions configured to perform a process including: obtaining raw data from a HBA assay performed on a plurality of samples, wherein the HBA assay is performed using a plurality of probes capable of detection of copy number losses or gains in a α-globin gene cluster region of each sample of the plurality of samples, and the raw data comprises HBA copy number data (e.g., MLPA copy number data) for the plurality of probes resolved by capillary electrophoresis for each sample of the plurality of samples; selecting a reference sample from the plurality of samples; calculating a first set of probe ratios for each sample of the plurality of samples based on the raw data from the HBA assay and the reference sample; identifying a predetermined number of reference samples to be combined as a synthetic reference sample for the plurality of samples based on the first set of probe ratios; generating the synthetic reference sample based on the predetermined number of reference samples; calculating a second set of probe ratios for each sample of the plurality of samples based on the raw data from the HBA assay and the synthetic reference sample; iteratively inputting the second set of probe ratios for each sample into a decision tree matrix; determining, by the decision tree matrix, a HBA genotype for each sample based on the second set of probe ratios for each sample and copy number calling thresholds for sample probe/reference probe ratios associated with each probe of the plurality of probes; and providing the HBA genotype for each sample. In some instances the technique further includes triggering performance of a confirmatory test on each sample of the plurality of samples that has a HBA genotype that is not normal or does not require manual review.

Advantageously, these approaches provide an HBA assay and genotyping technique that are capable of achieving minimal error rate in an environment such as a sequencing system with limited processing, memory and power resources. For example, the decision tree can be implemented with a low power budget (e.g., a simple tree of conditionals), and provides powerful non-linear classification capabilities of a multi-dimensional search space. Further, the non-linear classification may be used to gate whether or not confirmation testing should be performed on a sample, and consequently saves on costs of erroneously performing confirmation testing and increases robustness of the overall screening HBA assay.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. As used herein, when an action is "based on" something, this means the action is based at least in part on at least a part of the something.

It will be appreciated that the HBA genotyping techniques disclosed herein can be applied to assess other types of sequencing raw data as compared to the MLPA copy number data specifically described herein. It will also be appreciated that other assay methodologies and types of polymerase chain reaction (PCR) or multiplex (PCR) are contemplated to identify one or more loci within a given chromosome or gene region (e.g., chromosome 16 or α-globin region). For example, alternatively or additionally, reverse Dot-Blot Hybridisation (RDB), Southern blot (SB), or Gap-PCR may be used to identify one or more loci within chromosome 16 or the α-globin region.

II. HBA ASSAY TECHNIQUES

Figure 2:
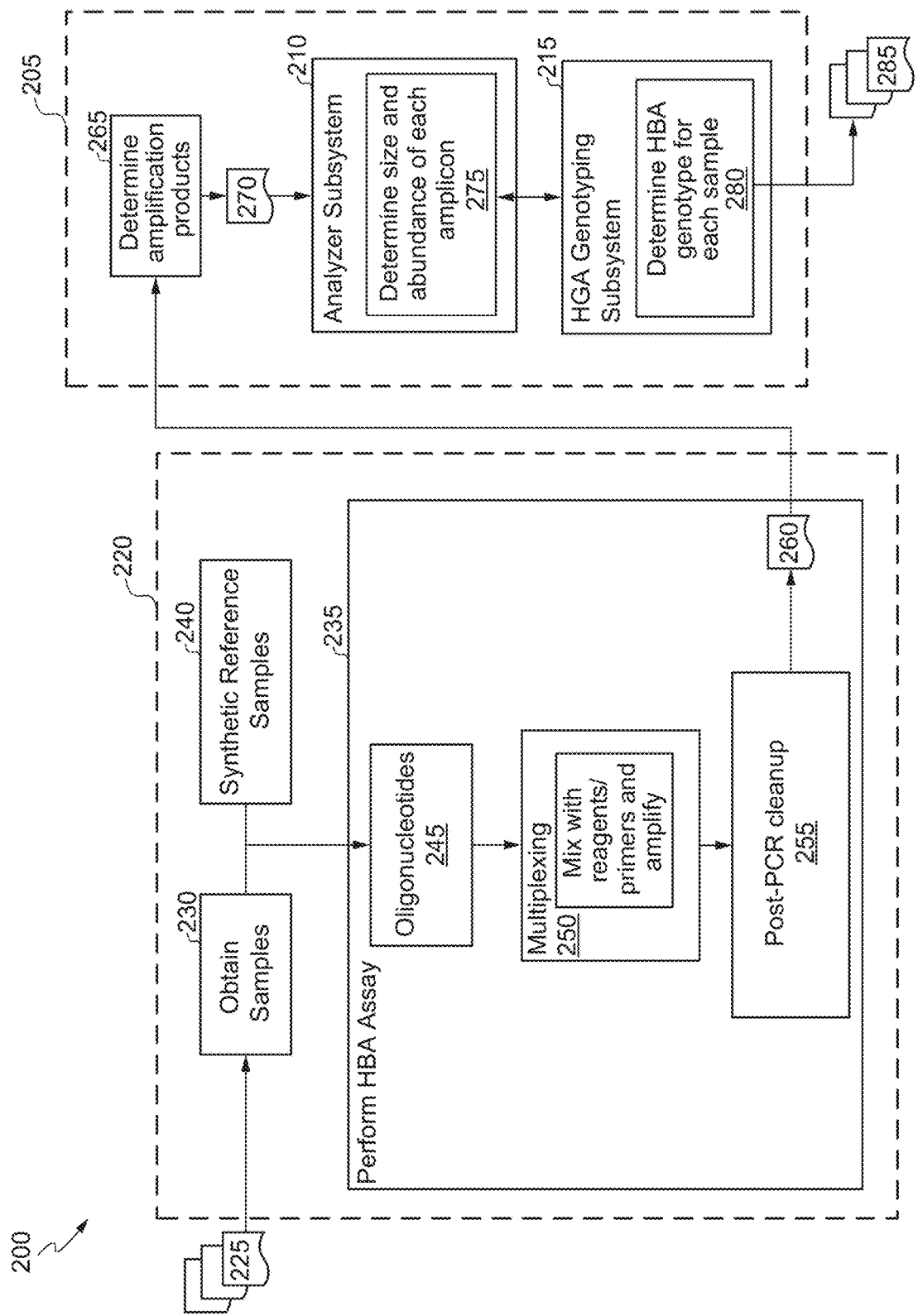
FIG. 2 shows a block diagram of an HBA assay platform in accordance with various embodiments.

One or more embodiments described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines. FIG. 2 shows a block diagram of an HBA assay platform 200 for detection of deletion(s) and/or duplication(s) in the α-globin region located on chromosome 16 as a potential cause for, screening tool, and/or clinical diagnosis of α-thalassemia, and illustrates modules, engines, or components (e.g., program, code, or instructions) executable by one or more processors that may be used to implement the various subsystems of a analyzer system 205 according to various embodiments. The modules, engines, or components may be stored on a non-transitory computer medium. As needed, one or more of the modules, engines, or components may be loaded into system memory (e.g., RAM) and executed by one or more processors the analyzer system 205. In the example depicted in FIG. 2, modules, engines, or components are shown implementing gene analyzer subsystem 210 and HBA genotyping subsystem 215.

FIG. 2 also illustrates a wet lab subsystem 220 including a laboratory where chemicals, drugs, or other material or biological matter are tested and analyzed requiring water, direct ventilation, and specialized piped utilities. The HBA assay platform 200 includes obtaining one or more samples 225 at block 230 within the wet lab subsystem 220. In some instances, the samples 225 comprise nucleic acid extracted from human cell lines. In some instances, the samples 225 comprise nucleic acid obtained from a male or female patient. In some instances, the samples 225 are nucleic acid extracted from whole blood, amniotic fluid, amniotic fluid cell cultures, chorionic villus sampling, or chorionic villus sample cell cultures obtained from a male or female patient. In certain instances, the sample or samples 225 have one or more genomic deletion(s), point mutation(s) and/or duplication(s) within the α-globin gene cluster region of chromosome 16.

At block 235 within the wet lab subsystem 220, an HBA Assay is performed including DNA analysis of the α-globin gene cluster region (HBA1/HBA2, OMIM 141800/141850, 16pter-16p13.3) is performed by targeting multiple distinct loci using a multiplex assay methodology 250 (e.g., multiplex PCR methodology). The multiplex assay methodology 250 detects genomic deletions and duplications involving this locus, including the seven most common types of α-thalassemia deletions ($\alpha^{3.7}$, $\alpha^{4.2}$, SEA, MED, THAI, FIL, and $\alpha^{20.5}$), as well the Constant Spring point mutation and the HBAx HS-40 promoter deletion. In certain instances, the HBA assay is used for: (i) a screening carriers of the $\alpha^{3.7}$, $\alpha^{4.2}$, SEA, MED, THAI, FIL, $\alpha^{20.5}$ and HS-40 deletions, (ii) identification of at-risk couples by screening partners of carriers for any of the HBA mutations, and/or (iii) targeted familial testing and prenatal testing for HBA deletions in which one or both parents have been determined to carry a pathogenic mutation as described herein. Confirmation testing may be performed by multiplex assay methodology and gel electrophoresis or Sanger sequencing.

Figure 3A:
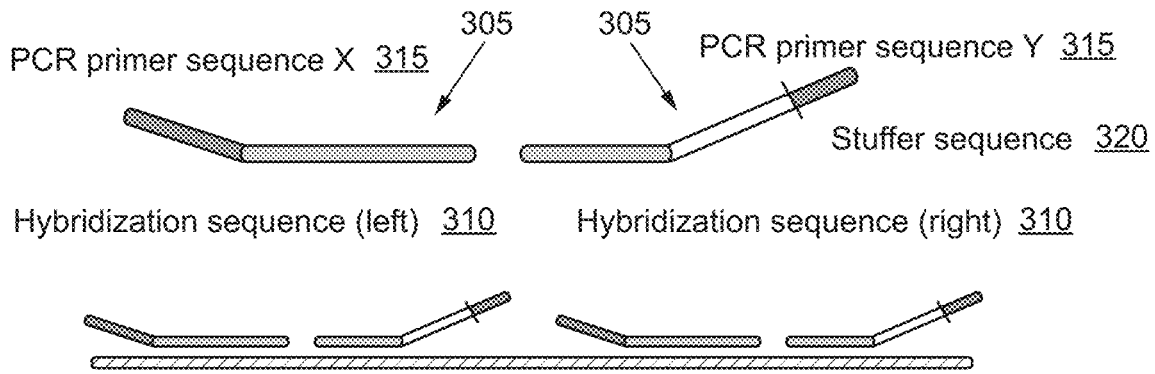
FIG. 3A shows an overview of MLPA assay chemistry in accordance with various embodiments.
Figure 3A:
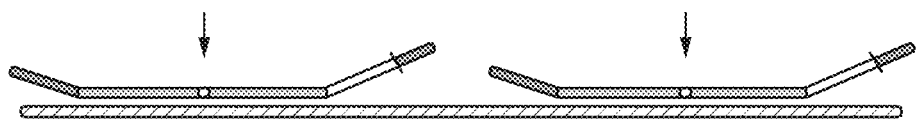
Figure 3A:
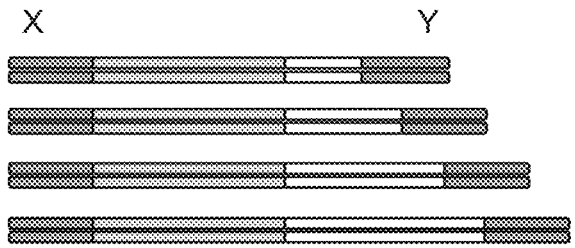
Figure 3A:
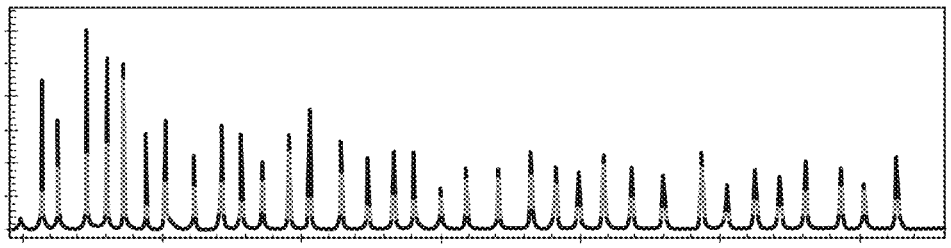

In various embodiments, the multiplex assay methodology 250 is MPLA technology (e.g., the MPLA methodology developed by MRC Holland—Product Description SALSA® MLPA® probemix P140-C1 HBA), which is a semi-quantitative, ligation-dependent multiplex PCR method that can determine copy number differences in the target region by measuring the relative signal intensity between the sample or samples 225 and a synthetic reference sample 240. The HBA assay uses a pool of MLPA oligonucleotides 245 such that a probe is formed when two oligonucleotides that hybridize immediately adjacent to each other at a target sequence are ligated together. As shown in FIG. 3A, each ligated probe 300 may be made up of two oligonucleotides 305 (e.g., from the pool of oligonucleotides 245) of which one end comprises a hybridization sequence 310 specific for a target sequence and another end comprises a PCR primer 315 (e.g., a labeled universal PCR primer) sequence for multiplexing. In certain instances, stuffer sequences 320 of different lengths may be used to allow for distinct probe sizes. After sample and reference denaturation, the oligonucleotides 305 are hybridized to the target sequences for a predetermined amount of time (e.g., 16-20 hours). Following hybridization, the two oligonucleotides 305 that hybridize to immediately adjacent sites are ligated together to form uniquely sized ligated probes 300. This reaction is highly specific and occurs when there are no gaps bigger than a nick between the two oligonucleotides 305. The ligated probes 300 are PCR amplified using the PCR primers 315. Ligated probes 300 that bind poorly to their target sequence or not at all due to SNPs or absence of target sequence will not amplify.

Figure 3B:
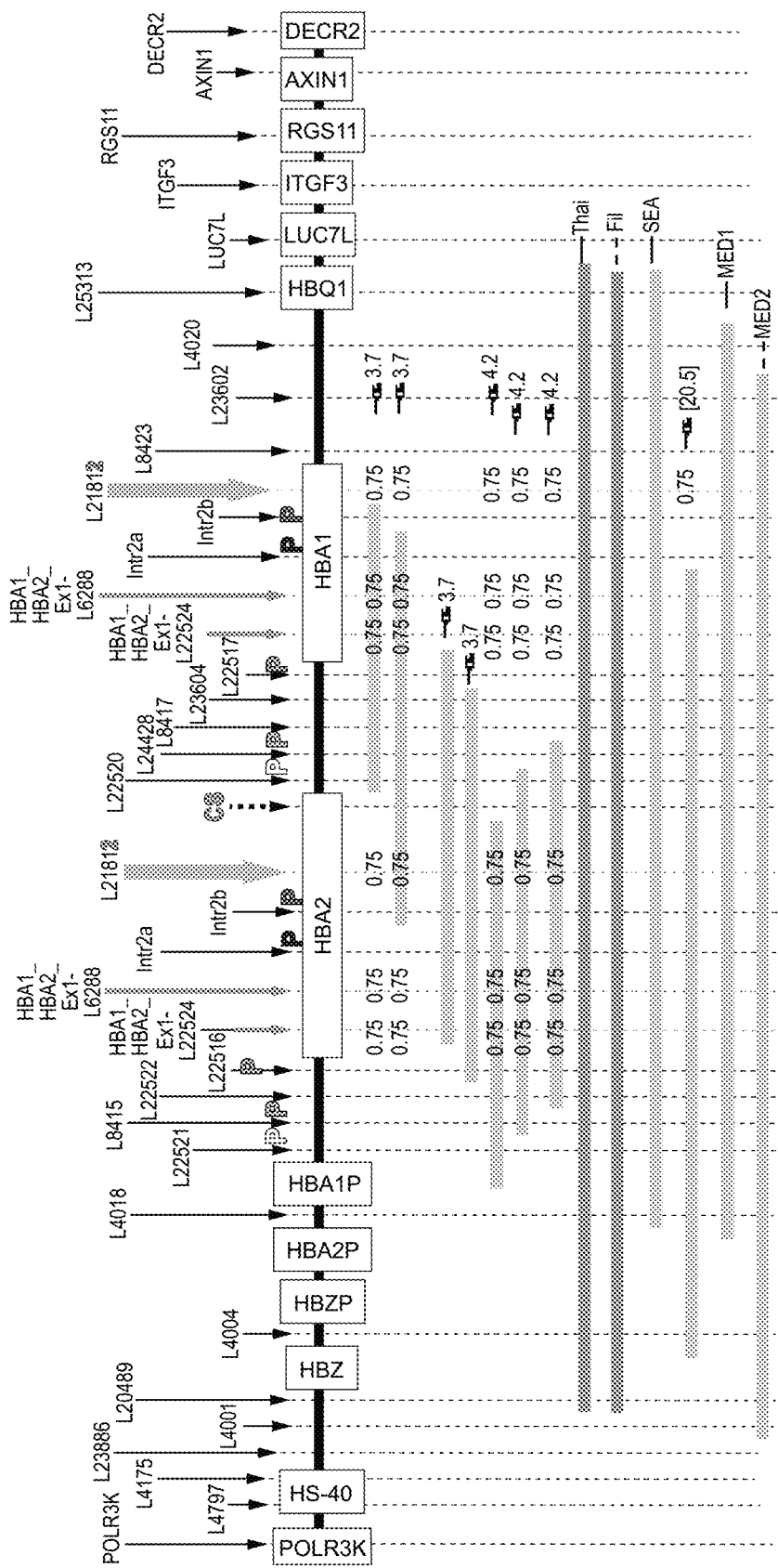
FIG. 3B shows locations of 34 α-globin gene cluster region probes and common HBA deletions in accordance with various embodiments.

In some embodiments, the HBA assay includes the use of 45 target-specific probes (amplification sizes 131-481 bases) that include 33 probes for detection of deletions and duplications in the α-globin gene cluster region and surrounding sequences and 1 probe for presence of the Hb Constant Spring point mutation. Of the 33 probes, there are 5 single probes that are specific for either HBA1 or HBA2 and 3 probes that target sequences in that are present in both genes; i.e., in a normal sample, 2 or 4 copies would be detected by a probe mapping to a unique sequence or a probe mapping to a sequence present in both HBA1 and HBA2, respectively. Due to the high homology and close proximity of the two genes, there are also 5 probe pairs that bind to different sequences in the same locations of the HBA1 and HBA2 genes such that one probe in a pair is specific for HBA1 and the other probe is specific for HBA2. These probe pairs are used to detect gene conversions, or polymorphisms, that have no clinical significance but could confound the genotyping call. When a polymorphism is present, the fold change for one probe in the pair would indicate a duplication, while the other, a deletion. The 45 target-specific probes further include 11 control probes that target reference sequences on other autosomal chromosomes besides chromosome 16, and are used for normalization of the 33 probes for detection of copy number changes in the HBA region. In some instances, quality control (Q- and D-fragments) and gender-specific fragments, which are single oligonucleotides, may be included to ensure that the MLPA chemistry worked as expected. Locations of probes that detect variants in the α-globin gene cluster region and surrounding sequences as well as the locations for the targeted deletions in this test are schematically shown in FIG. 3B. Shown are locations for the paired probes (P) that can detect polymorphisms due to gene conversions between HBA1 and HBA2, the probes mapping to both HBA1 and HBA2, (bold arrows), and the probe for Hb Constant Spring (CS). The FIL and THAI deletions are detected by the same probes and require multiplex PCR for differentiation. In some instances, the deletion boundaries for $\alpha^{3.7}$, $\alpha^{4.2}$ and MED can vary and their detection may involve different probes.

At optional block 255, post-PCR cleanup may be performed on the PCR products (e.g., the amplified ligated probes). In some instances, the post-PCR cleanup includes mixing the PCR products with magnetic beads, washing with a wash solution such as 70% ethanol, air drying, and eluting purified PCR products 260 to boost the signal-to-noise ratio. After amplification and post-PCR cleanup, the purified PCR products 260 may be loaded onto analyzer system 205 (e.g., a fluorescence-based separation instrument system) for downstream processing.

At block 265, the multiplex assay products or optional purified PCR products 260 are resolved using capillary electrophoresis, detected using the label, e.g. a fluorescent dye, and output as raw data 270 comprising HBA copy number data. In some instances, the raw data 270 may be generated, collected, and stored on the analyzer system 205 in a memory storage device. At block 275, the analyzer subsystem 210 obtains the raw data 270 for each sample from the analyzer system 205, determines sizing of the amplicons, and automatically selects a normalized sample with the least variability in peak height ratios and no detected deletions/duplications as a reference sample. The analyzer subsystem 210 normalizes the raw peak signals for each test probe (normal probe) to that of control probes in order to minimize any preferential amplification of smaller fragments. For example, the control probe peak heights, or signals, in a test sample may be compared to the corresponding control probe peak heights in the reference sample. Variability in the ratio of signals between the two are calculated as the control probe standard deviation, and values of the control probe standard deviation greater than a predetermined threshold (e.g., 0.125 threshold) may cause the sample to fail. The analyzer subsystem 210 may also check the quality control D- and Q-fragments to ensure that the PCR reaction meets predetermined quality criteria and anything outside the predetermined quality criteria may cause the sample to fail.

The normalized probe peak signals of test probes for the samples that did not fail are then compared to the peak signals for the corresponding test probes in the reference sample. Relative probe ratios, or fold changes between the sample and reference probe signals are then calculated by the analyzer subsystem 210, and any changes to the sample probe/reference probe ratio that are outside a normal range (e.g., copy number calling threshold) may be identified by the analyzer subsystem 210 as a deletion or duplication. Thus, the relative probe ratio, or fold change, of a sample with no deletions or duplications relative to a reference sample is ~1, and a decrease or increase in the probe ratio beyond a copy number calling threshold may be interpreted as a deletion or duplication, respectively, of the target sequence. The analyzer subsystem 210 may generate and export an initial results file including the relative probe ratio, or fold change, of each sample 225.

At block 280, the relative probe ratio data calculated on the analyzer subsystem 210 is analyzed by the HBA genotyping subsystem 215 for aberrant probe ratio patterns based on deletion(s) and/or duplications(s) to identify genotypes targeted for testing. More specifically, the HBA genotyping subsystem 215 is configured to serve several purposes: a) to check the data quality; b) to select samples for creating a synthetic reference with a negative selector tool; and c) to sequentially parse the relative probe ratio data calculated by the analyzer subsystem 210 through a decision tree matrix for genotype calling. To maximize the number of tests that can be run in a batch and since ~85-90% of the samples for carrier screening will be negative for an HBA deletion or duplication, the negative selector tool of the HBA genotyping subsystem 215 was developed to provide a technical advantage to identify three to six best quality samples that have the best quality metrics and are negative for any copy number variation (no deletions/duplications) for the control sample selection application in the analyzer subsystem 210. The three to six best quality samples are then communicated and/or selected by the control sample selection application in the analyzer subsystem 210, and the analyzer subsystem 210 combines the three to six best quality samples to create a synthetic reference sample. The relative probe ratio, or fold change for each sample 225 are then recalculated by the analyzer subsystem 210 using this synthetic reference sample. The recalculation takes into account samples from all parts of the plate, so in addition to maximizing the number of samples that can be run per plate, it the synthetic reference sample normalizes fold-change ratios across the plate, making it less likely that samples will fail. The analyzer subsystem 210 may generate and export a new results file including the new calculated relative probe ratio, or fold change of each sample 225. The HBA genotyping subsystem 215 uses these new calculated relative probe ratios, or fold changes and the decision tree matrix to classify and/or identify the HBA genotypes in each sample 225.

In various embodiments, after checking the new calculated relative probe ratios, or fold changes for data quality, the HBA genotyping subsystem 215 uses copy number calling thresholds to identify regions of copy number losses or gains with probes which are involved in multiple abnormal genotypes and sorts each sample into a normal, polymorphic or copy number variation (CNV) category. The CNV samples may then be classified as either large targeted deletions, duplications or other. Samples in the large targeted deletion group are determined for zygosity and further classified as SEA, FIL/THAI, MED or α-20.5. Samples that are heterozygous are further checked for the $\alpha^{3.7}$ and $\alpha^{4.2}$ deletions. Those in the 'other' category may also be checked for the $\alpha^{3.7}$ and $\alpha^{4.2}$ deletions, and if either are detected, for zygosity. At this point, all samples should have been classified as either a targeted genotype or 'other'. The HBA genotyping subsystem 215 then compares the combination of probes against a table that has each possible scenario to identify compound heterozygotes for the targeted deletions and duplications. All samples may also be analyzed by the HBA genotyping subsystem 215 for the HS-40 deletion and the Hb Constant Spring point mutation, and any positive results are concatenated onto the previously determined genotype. Samples that are still classified as 'other' are flagged for review by a healthcare professional such as a clinical director, thereby ensuring that the HBA genotyping subsystem 215 will not miss any clinically important results, targeted or not.

The HBA genotype of each sample and an optional risk result for each sample are output by the analyzer system 205 as a final result 285. In some instances, all threshold and QC parameters and the decision tree matrix used by the analyzer subsystem 205 and the HBA genotyping subsystem 215 are maintained in one or more separate configuration files and can be used across any number of HBA PCR assays.

III. HBA GENOTYPING TECHNIQUES

Figure 4:
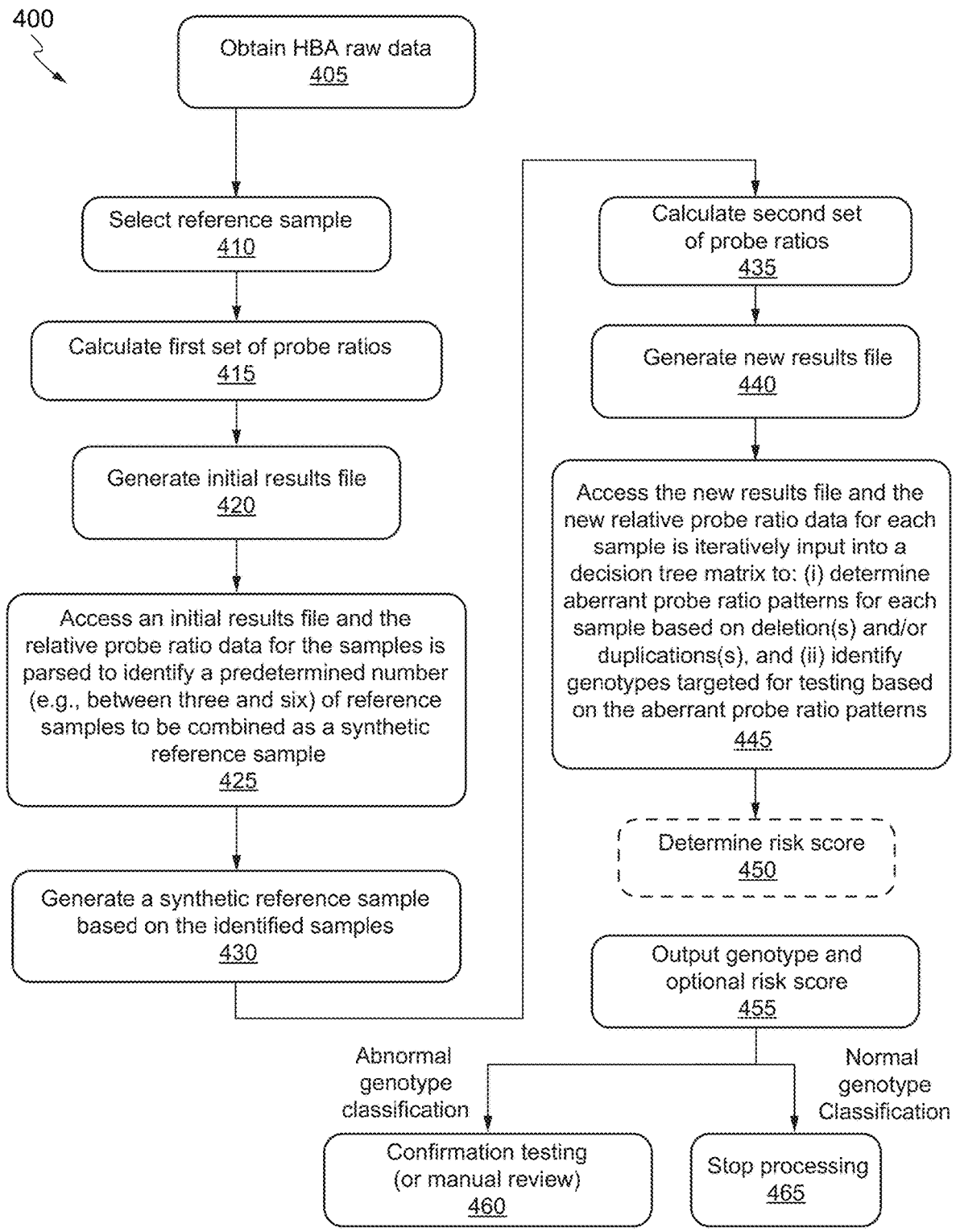
FIG. 4 shows an exemplary flow for an HBA assay and HBA genotyping using an HBA assay platform and genotyping techniques in accordance with various embodiments.

FIG. 4 illustrates a process 400 for HBA genotyping using an HBA assay platform and genotyping techniques (e.g., the HBA assay platform 200 described with respect to FIG. 2). Process 400 begins at block 405, where raw data is obtained from an HBA assay performed on a plurality of samples. In some instances, the HBA assay is performed using a plurality of probes (e.g., ligated probes) capable of detection of copy number losses or gains (e.g., deletions, duplications and Hb Constant Spring Point Mutation) in the α-globin gene cluster region of each sample of the plurality of samples. The plurality of probes may include one or more control probes and one or more test probes. In some instances, the raw data comprises HBA copy number data for the plurality of probes resolved by capillary electrophoresis for each sample of the plurality of samples. At block 410, a reference sample is selected from the plurality of samples. The reference sample may be selected to obtain a reference sample that has the least variability among the plurality of probes and no copy number variation (e.g., no deletion(s) and/or duplication(s)) based on the raw data for the plurality of probes.

In some instances, prior to selection of a reference probe, the quality of the raw data is checked. The quality check of the raw data may include confirming quality of the raw data using one or more parameters listed in Table 1. In some instances, one or more of the following quality checks are performed and the quality of the raw data is assessed based on the result(s) of the one or more quality checks: (i) a total probe number being equal to a predetermined number of total probes such as 45, (ii) a test (normal) probe number being equal to a predetermined number of test probes such as 33, (iii) a control probe number being equal to a predetermined number of control probes such as 11, (iv) peak signals being greater than or equal to a predetermined peak height threshold (e.g., greater than or equal to 200 RFU after normalization), (v) the Q-fragments (single oligonucleotides (not ligated probes) that will preferentially amplify when the DNA amount is too low or ligation fails) represent ≤a predetermined threshold, e.g., 33% of signal for 92 nt benchmark fragment, and (vi) the D-fragments (single oligonucleotides (not ligated probes) that will preferentially amplify when the denaturation reaction is incomplete) represent a predetermined threshold, e.g., 50% of signal for 92 nt benchmark fragment. When the quality of the raw data fails, then the process may stop and optionally request the HBA assay be performed again to obtain new raw data. When the quality of the raw data passes, then the process may continue.

TABLE 1

Quality Metrics and Thresholds used in this Study

| Parameter | Description/Purpose | Threshold |
| --- | --- | --- |
| Total Probe Number | All (normal and control) probes in the assay; used to identify normal samples (0 CNV probes) | Must equal 45 |
| Normal Probe Number | Normalized probes that target the α-globin gene cluster region and surrounding sequences | Must equal 33 |
| Control Probe Number | Control probes that target stable (0 CNV) sequences on autosomal chromosomes besides chr 16; used to normalize signals within a sample and assess normalized probe data between a sample and reference | Must equal 11 |
| Peak Height Threshold | Minimum RFU threshold of fluorescent signal peak height required for detection | ≥200 RFU after normalization |
| MLPA Lane Score | Signal-to-noise quality of the normalized traces | >10 |
| Q-fragments | Single oligonucleotides (not ligated probes) that will preferentially amplify when the DNA amount is too low or ligation fails | ≤33% of signal for 92 nt benchmark fragment |
| D-fragments | Single oligonucleotides (not ligated probes) that will preferentially amplify when denaturation reaction is incomplete | ≤50% of signal for 92 nt benchmark fragment |
| Copy Number Calling Threshold | Relative signal between normalized sample probe and corresponding reference probe; used to detect deletions and duplications; also referred to as relative probe ratio or fold change v. reference in this document | Deletion < 0.75 < Normal < 1.30 < Duplication |
| Copy Number Calling Threshold for Duplicated Probes | Same as copy number calling threshold except 4 copies detected in a normal sample due to duplicated probes recognizing homologous sequences in HBA1 and HBA2 | Deletion < 0.87 < Normal < 1.12 < Duplication |
| Control Probe Standard Deviation | Measure of control probe variability in the reference sample when compared to the corresponding control probe in the test sample | <0.125 |
| Hb Constant Spring detection | A signle probe is used to detect presence of the mutation; does not determine zygosity | Constant Spring mutant probe peak height ≥10% of mean peak height of all control probes in a sample |

At block 415, a first set of probe ratios are calculated for each sample of the plurality of samples (in some instances, the first set of probe ratios is not calculated for the reference sample). In some instances, the calculating the first set of probe ratios comprises: (i) comparing the control probe peak heights, or signals, in each sample to corresponding control probe peak heights in the selected reference sample, (ii) calculating variability in the signals between the control probe peak heights, or signals, in each sample and the control probes of the reference sample as the control probe standard deviation, (iii) determining a sample of the plurality of samples fails when the control probe standard deviation is greater than or equal to a predetermined threshold (e.g., ≥0.125 threshold), (iv) determining a sample of the plurality samples does not fail when the control probe standard deviation is less than a predetermined threshold (e.g., <0.125 threshold), and (v) for each sample that does not fail, comparing the test probe peak heights, or signals, in the sample to corresponding test probe peak heights in the selected reference sample, and calculating a probe ratio between the test probe peak heights, or signals, in the sample and the corresponding test probe peak heights in the selected reference sample.

At block 420, an initial results file is generated and output that includes the first set of probe ratios calculated for each sample. The first set of probe ratios includes the relative probe ratio, or fold change, of each sample calculated in step 415 that did not fail (and optionally is not the reference sample). At block 425, the initial results file is accessed and the first set of probe ratios for the samples is parsed to identify a predetermined number (e.g., between three and six) of reference samples to be combined as a synthetic reference sample for the plurality of samples. In certain instances, the reference samples are identified based on quality metrics and copy number variation. For example, the identified reference samples should be negative for any copy number variation (e.g., have no probes out of normal range based on the copy number calling thresholds, and thus no deletions or duplications), pass all probe number metrics, and have the lowest control probe standard deviation metrics on the plate of samples. A list may be generated that comprises the identified reference samples and a synthetic reference sample file is generated and output that includes the list of the identified samples. At block 430, the synthetic reference sample file is accessed or uploaded to a computing system, and a synthetic reference sample is generated based on the identified reference samples within the list. In some instances, the synthetic reference sample is created as a functional concatenation of peak heights, or signals, for each of the identified samples within the list. For example, the synthetic reference sample may be a mean, median, or mode of the peak heights, or signals, for each of the identified samples within the list.

At block 435, a second set of probe ratios are calculated for each sample of the plurality of samples. In some instances, the calculating the second set of probe ratios comprises: (i) comparing the control probe peak heights, or signals, in each sample to corresponding control probe peak heights in the synthetic reference sample, (ii) calculating variability in the signals between the control probe peak heights, or signals, in each sample and the control probes of the synthetic reference sample as the control probe standard deviation, (iii) determining a sample of the plurality of samples fails when any variability metrics are greater than or equal to a predetermined threshold (e.g., ≥0.125 threshold), (iv) determining a sample of the plurality of samples does not fail when none of the variability metrics are greater than or equal to a predetermined threshold (e.g., ≥0.125 threshold), and (v) for each sample that does not fail, comparing the test probe peak heights, or signals, in the sample to corresponding test probe peak heights in the synthetic reference sample, and calculating a probe ratio between the test probe peak heights, or signals, in the sample and the corresponding test probe peak heights in the synthetic reference sample.

At block 440, a new results file is generated and output that includes new relative probe ratio data for each sample. The new relative probe ratio data includes the relative probe ratio, or fold change, of each sample calculated in step 435 that did not fail. At block 445, the new results file is accessed and the new relative probe ratio data for each sample is iteratively input into a decision tree matrix to: (i) determine aberrant probe ratio patterns for each sample based on deletion(s) and/or duplications(s), and (ii) identify genotypes targeted for testing based on the aberrant probe ratio patterns. The determination of the aberrant probe ratio patterns and identification of genotypes targeted for testing may comprise identifying, by the decision tree matrix, one or more regions of copy number losses or gains (e.g., deletion(s) and/or duplications(s)) based on the new relative probe ratio data for the plurality of probes and normal ranges or the copy number calling thresholds for the sample probe/reference probe ratios associated with each probe. For example, any changes to the sample probe/reference probe ratios that are outside a normal range (e.g., the copy number calling threshold) are identified as a deletion or duplication and may be used to identify one or more regions of copy number losses or gains. The determination of the aberrant probe ratio patterns may further comprise classifying the sample as normal, having a copy number variation (CNV), or as polymorphic based on the identified one or more regions of copy number losses or gains. For example, if a sample has no probes out of normal range, then the sample may be classified as normal. If a sample has one or more probes out of normal range, then the sample may be classified as CNV. For samples with one or more probes out of normal range, if none of the probes out of normal range are within a subset of probes indicative of deletions (e.g., a subset of deletion probes identified as being important for calling a CNV), then the sample may be classified as polymorphic.

The determination of the aberrant probe ratio patterns and identification of genotypes targeted for testing may further comprise sub classifying the sample classified as having a CNV as large targeted deletions, duplications or 'other' based on the identified one or more regions of copy number losses or gains. For example, if a sample classified as having a CNV has one or more probes indicative of large targeted deletions that are out of normal range, then the sample may be further classified as having large targeted deletions. If a sample classified as having a CNV has one or more probes indicative of duplications that are out of normal range, then the sample may be further classified as having duplications. If a sample classified as having a CNV does not have one or more probes indicative of large targeted deletions or duplications that are out of normal range, then the sample may be further classified as 'other'.

The determination of the aberrant probe ratio patterns and identification of genotypes targeted for testing may further comprise determining deletion status and zygosity and duplication status for samples in the CNV group (e.g., homozygous or heterozygous deletion) based on one or more probes indicative of zygosity, and further classifying the samples for one of the following deletions, or a duplication: $\alpha^{3.7}$ and $\alpha^{4.2}$ based on one or more probes indicative of deletions $\alpha^{3.7}$ and $\alpha^{4.2}$ that are out of normal range. Large deletions defined as deletions that encompass both the HBA1 and HBA2 genes. Samples in the large targeted deletion group may be determined for zygosity (e.g., homozygous or heterozygous large deletions) based on one or more probes indicative of zygosity, and further classified for one of the following deletions: SEA, FIL/THAI, MED or $\alpha^{20.5}$, or the $\alpha^{3.7A}/\alpha^{4.2C}$ deletion of indeterminate phasing based on one or more probes indicative of deletions SEA, FIL/THAI, MED, $\alpha^{20.5}$, $\alpha^{3.7A}/\alpha^{4.2C}$ that are out of normal range. Samples classified as heterozygous large deletions may be further classified for the smaller $\alpha^{3.7}$ and $\alpha^{4.2}$ deletions based on one or more probes indicative of deletions $\alpha^{3.7}$ and $\alpha^{4.2}$ that are out of normal range. At this point, a sample should have been classified as either a targeted genotype or 'other'. Examples of targeted genotypes a result of this process, the result implication, and possible clinical interpretation are provided in Table. 2.

not miss any clinically important results, targeted or not. Moreover, all samples (those classified as normal, CNV, and polymorphic) may also be analyzed for the HIS-40 deletion and the Hb Constant Spring point mutation based on one or more probes indicative the HIS-40 deletion and the Hb Constant Spring point mutation, that are out of normal range, and any positive results may be concatenated onto the previously determined targeted or non-targeted genotype.

Optionally at block 450, the genotype of each sample determined in block 445 may be used to determine a risk score(s) for a subject associated with the sample. The risk score(s) may identify: (i) a risk of the subject being a carrier of the $\alpha^{3.7}$, $\alpha^{4.2}$, SEA, MED, THAI, FIL, $\alpha^{20.5}$ and HS-40 deletions and Hb Constant Spring point mutation, (ii) a risk for couples identified as being a carrier of the $\alpha^{3.7}$, $\alpha^{4.2}$, SEA, MED, THAI, FIL, $\alpha^{20.5}$ and HS-40 deletions and Hb Constant Spring point mutation, and/or (iii) a risk of a fetus inheriting the $\alpha^{3.7}$, $\alpha^{4.2}$, SEA, MED, THAI, FIL, $\alpha^{20.5}$ and HS-40 deletions and Hb Constant Spring point mutation. At

TABLE 2

Possible MLPA Results and Their Implications for Mutations Targeted in the Test

| Result* | Genotype | Result Implication | Clinical Interpretation |
|---|---|---|---|
| No deletions or CS point mutation (Normal) | $\alpha\alpha/\alpha\alpha$ | 2 copies of HBA1 and HBA2 present and expressed normally | NEG |
| Polymorphism | $\alpha\alpha/\alpha\alpha$ | 2 copies of HBA1 and HBA2 present and expressed normally | NEG |
| Additional copy of $\alpha^{4.2}$ or $\alpha^{3.7}$ | $\alpha\alpha\alpha/\alpha\alpha$ | 3 copies of HBA1 and 2 copies of HBA2 present OR 3 copies of HBA2 and 2 copies of HBA1 present | NEG |
| HET, $\alpha^{3.7}$ deletion or $\alpha^{4.2}$ deletion | $-\alpha/\alpha\alpha$ | 1 copy of either HBA1 or HBA2 | Silent carrier |
| HS-40 promoter deletion | $\alpha\alpha/\alpha\alpha$ | 2 copies each of HBA1 and HBA2 present but low/no expression for HBA1 and HBA2 | Carrier with α-thal trait |
| HOM of either $\alpha^{3.7}$ deletion or $\alpha^{4.2}$ deletion | $-\alpha/-\alpha$ | 0 copies of either HBA1 or HBA2 | Carrier with α-thal trait |
| HET α-3.7 deletion in trans $\alpha^{4.2}$ deletion | $-\alpha/-\alpha$ | 1 copy each of HBA1 and HBA2 in trans | Carrier with α-thal trait |
| HET SEA, FIL, THAI, MED or $\alpha^{20.5}$ deletion | $--/\alpha\alpha$ | 1 copy each of HBA1 and HBA2 in cis | Carrier with α-thal trait |
| HET CS SNV | $\alpha\alpha^{CS}/\alpha\alpha$ | Low expression of HBA2 on one chromosome | Carrier with α-thal trait |
| HOM CS SNV | $\alpha\alpha^{CS}/\alpha\alpha^{CS}$ | No or very low expression of HBA2 | Carrier with α-thal trait |
| HET $\alpha^{3.7}$ or $\alpha^{4.2}$ deletion AND HET SEA, FIL, MED, THAI, or $\alpha^{20.5}$ | $--/-\alpha$ | 1 copy of HBA1 or HBA2 | Affected with HbH disease |
| SEA, FIL, THAI, MED or $\alpha^{20.5}$ deletion in trans with Constant Spring SNV | $--/\alpha^{CS}\alpha$ | 1 copy of HBA1 and CS point mutation in cis | Affected with HbH disease |
| HOM SEA, FIL, THAI, MED or $\alpha^{20.5}$ deletion | $--/--$ | 0 copy of HBA1 and HBA2 | Affected with Hb Bart's hydrops fetalis |
| HET SEA, FIL, THAI, MED or $\alpha^{20.5}$ deletion in any combination | $--/--$ | 0 copy of HBA1 and HBA2 | Affected with Hb Bart's hydrops fetalis |
| HET SEA, FIL, THAI, MED or $\alpha^{20.5}$ deletion in trans with HET HS-40 deletion | $--/\alpha\alpha$ | 1 copy each of HBA1 and HBA2 in cis expressed at low or no levels | Affected with Hb Bart's hydrops fetalis |

*Note:
The MLPA technology cannot detect copy number neutral inversions or translocations. This table lists scenarios only for the targeted mutations tested and does not include situations that would trigger review by a healthcare provider such as a clinical director. HET, heterozygous; HOM, homozygous; CS SNV, Constant Spring single nucleotide variant The determination of the aberrant probe ratio patterns and identification of genotypes targeted for testing may further comprise comparing the new relative probe ratio data against a table that has every possible scenario to identify non-target genotypes such as compound heterozygotes for the targeted deletions and duplications. Samples that are still classified as 'other' after the table comparison may be flagged for review by a healthcare provider such as a clinical director, thereby ensuring that the genotyping technique will block 455, the genotype of each sample determined in block 445 and optional risk score(s) determined in block 450 may be output. The output of the genotype of each sample and optional risk score(s) may comprise providing an end user with the output and/or recording the output in a storage device (e.g., displaying the output on a user interface and/or storing the output in a results file of a database). At block 460, when the genotype of the sample determined in block 445 indicates one or more of the $\alpha^{3.7}$, $\alpha^{4.2}$, SEA, MED, THAI, FIL, $\alpha^{20.5}$ and HS-40 deletions and Hb Constant Spring point mutation are assigned to the sample, confirmation testing may be performed on the sample. Confirmation testing may be performed by multiplex assay methodology and gel electrophoresis or Sanger sequencing. When the genotype of the sample is undetermined in block 445, manual review may be performed for the sample. At block 465, when the genotype of the sample determined in block 445 indicates a normal classification is assigned to the sample, processing of a sample is stopped. As such, the non-linear classification of the decision tree matrix may be used to gate whether or not confirmation testing should be performed on a sample, and consequently saves on costs of erroneously performing confirmation testing and increases robustness of the overall screening HBA assay.

Figure 5:
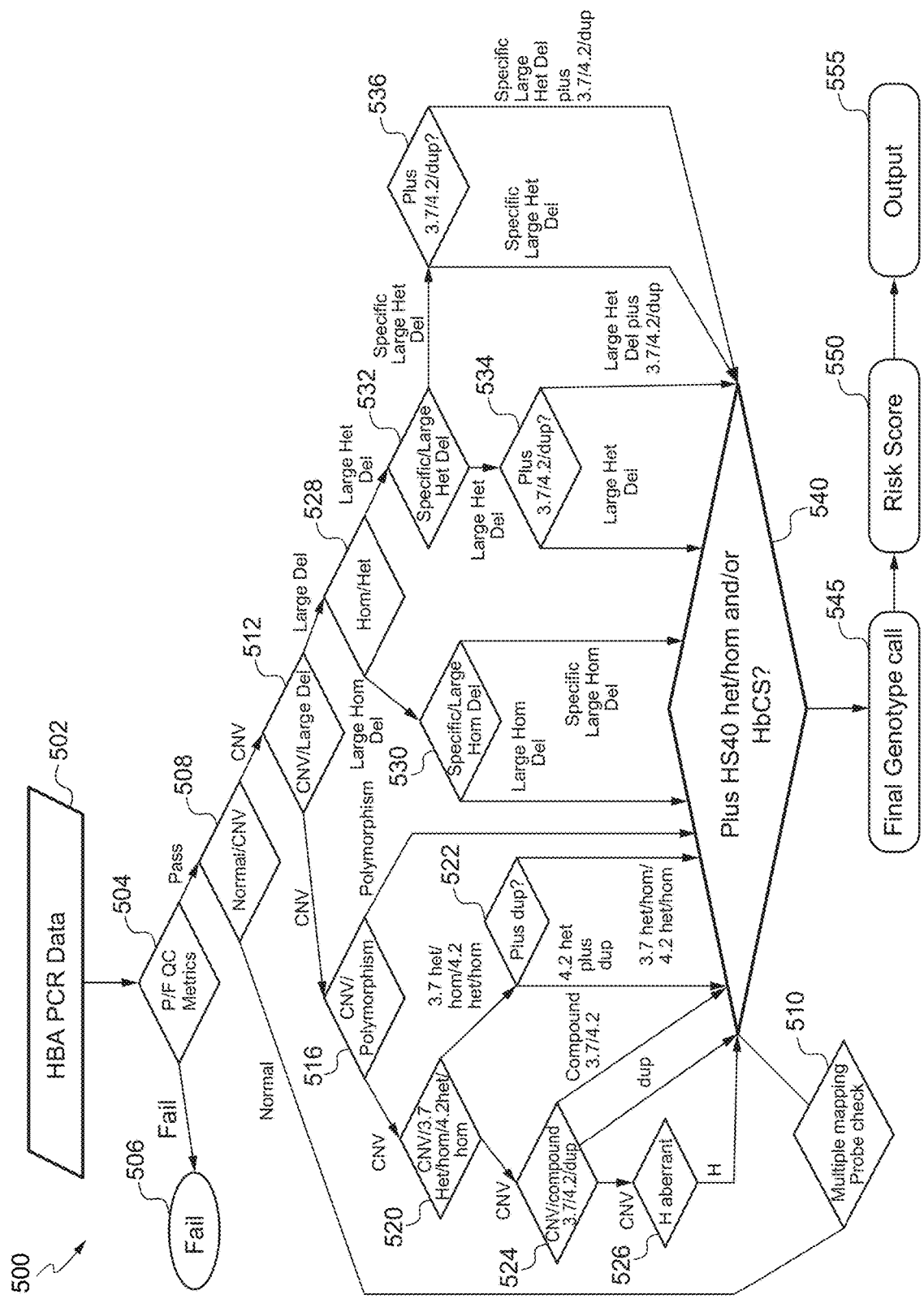
FIG. 5 shows an exemplary flow for HBA genotyping using an HBA assay platform and genotyping techniques in accordance with various embodiments.

FIG. 5 shows a decision tree matrix 500 illustrating genotyping techniques that may be implemented to perform HBA genotyping of one or more samples. At block 502, a new results file is accessed and raw data including HBA copy number data for each sample of a plurality of samples is iteratively input into a decision tree matrix to: (i) determine aberrant probe ratio patterns for each sample based on deletion(s) and/or duplications(s), and (ii) identify genotypes targeted for testing based on the aberrant probe ratio patterns. The raw data includes new relative probe ratio data (as discussed with respect to steps 435, 440, and 445 in FIG. 4) for each sample obtained based on a synthetic reference sample (as discussed with respect to steps 425 and 430 in FIG. 4). The new relative probe ratio data includes the relative probe ratio, or fold change, of each probe of a plurality of probes used to analyze the α-globin gene cluster region of each sample of the plurality of samples. In some instances, the new relative probe ratio data is obtained from an HIBA assay performed using a plurality of probes (e.g., ligated probes), which are capable of detection of deletions, duplications and Hb Constant Spring Point Mutation in the α-globin gene cluster region of each sample of the plurality of samples, as discussed with respect to FIGS. 1 and 4. Table 3 provides an exemplary list of a plurality of probes that may be used to perform the HIBA assay and genotyping. The plurality of probes include one or more control probes (e.g., Ctrl_5q31) and one or more test probes (e.g., HBA_HBA1).

TABLE 3

List of Probes-Total of 45 probes including 11 control probes and 34 test probes

| Manufacturer Probe Number | Probe Name | HG19 coordinates | Probe Number |
|---|---|---|---|
| 11435-L12163 | *Ctrl_1q41 | chr1:215813987-215814050 | C05 |
| 15318-L17117 | *Ctrl_2q33 | chr2:200188562-200188633 | C11 |
| 03272-L02709 | *Ctrl_3q29 | chr3:193412522-193412595 | C09 |
| 03075-L19996 | *Ctrl_5p15 | chr5:9437899-9437965 | C06 |
| 00797-L13645 | *Ctrl_5q31 | chr5:132009710-132009772 | C01 |
| 07641-L07326 | *Ctrl_8p23 | chr8:11612591-11612664 | C02 |
| 05846-L11214 | *Ctrl_10q26 | chr10:131557466-131557538 | C03 |
| 00547-L00116 | *Ctrl_11q22 | chr11:102220951-102221012 | C08 |
| 11331-L12056 | *Ctrl_12p13 | chr12:6101020-6101086 | C04 |
| 03250-L02687 | *Ctrl_13q14 | chr13:52511732-52511800 | C07 |
| 07607-L07292 | *Ctrl_15q26 | chr15:99482536-99482612 | C10 |
| 19236-L25316 | POLR3K_TeloHBA | chr16:97132-97217 | 1 |
| 04799-L04797 | HS-40_HS-40 | chr16:163528-163595 | 2 |
| 04800-L04175 | HS-40_HS-40_2 | chr16:163685-163749 | 3 |
| 04926-L23886 | HBA_HBZ_2 | chr16:193637-193702 | 4 |
| 04622-L04001 | HBA_HBZ | chr16:199336-199407 | 5 |
| 17214-SP0457-L20489 | HBA_HBZ_3 | chr16:202592-202698 | 6 |
| 04624-L04004 | HBA_HBZHBZP1 | chr16:209467-209540 | 7 |
| 04637-L04018 | HBA_HBAP2HBAP1 | chr16:217274-217344 | 8 |
| 18097-L22521 | HBA_HBA2_4 | chr16:219798-219876 | 9 |
| 18090-L08415 | HBA_HBA2_3 | chr16:220313-220396 | 10 |
| 18098-L22522 | HBA_HBA2 | chr16:221951-222031 | 11 |
| 18092-L22516 | HBA_HBA2_2 | chr16:222190-222260 | 12 |
| 18099-L22524 | HBA1HBA2_ex1_2 | chr16:222841-222896 | 13 |
| 18881-L06288 | HBA1HBA2_ex1 | chr16:222921-222988 | 14 |
| 08498-L08422 | HBA2_intron2 | chr16:223362-223420 | 15 |
| 04633-L23748 | HBA2_intron2_2 | chr16:223427-223490 | 16 |
| 15857-L21812 | HBA1HBA2_ex3 | chr16:223484-223544 | 17 |
| S0585-SP0043-L09493 | HBA2_mutation | chr16:223569-223657 | 18 |
| 18096-L22520 | HBA_HBA1_2 | chr16:224084-224160 | 19 |
| 18880-L24428 | HBA_HBA1_3 | chr16:224602-224690 | 20 |
| 08494-L08417 | HBA_HBA1_5 | chr16:225160-225221 | 21 |
| 14855-L23604 | HBA_HBA1_8 | chr16:225728-225789 | 22 |
| 18093-L22517 | HBA_HBA1_4 | chr16:226018-226093 | 23 |
| 18099-L22524 | HBA1HBA2_ex1_2 | chr16:226644-226700 | 13 |
| 18881-L06288 | HBA1HBA2_ex1 | chr16:226725-226792 | 14 |
| 08498-L21607 | HBA1_intron2 | chr16:227166-227223 | 26 |
| 04633-L23600 | HBA1_intron2_2 | chr16:227237-227301 | 27 |
| 15857-L21812 | HBA1HBA2_ex3 | chr16:227295-227353 | 17 |
| 08499-L23594 | HBA_HBA1 | chr16:227572-227638 | 29 |
| 04638-L23602 | HBA_HBA1_6 | chr16:227890-227962 | 30 |
| 04639-L04020 | HBA_HBA1_7 | chr16:229744-229814 | 31 |
| 19233-L25313 | HBQ1_ex3 | chr16:231170-231236 | 32 |
| 15859-L21960 | LUC7L_CentroHBA | chr16:256304-256385 | 33 |
| 17227-L20554 | ITFG3_CentroHBA | chr16:289853-289926 | 34 |

TABLE 3-continued

List of Probes-Total of 45 probes including 11 control probes and 34 test probes

| Manufacturer Probe Number | Probe Name | HG19 coordinates | Probe Number |
|---|---|---|---|
| 18102-L20488 | RGS11_CentroHBA | chr16:321757-321830 | 35 |
| 17212-L13393 | AXIN1_CentroHBA | chr16:338106-338166 | 36 |
| 17613-L23601 | DECR2_CentroHBA | chr16:457523-457589 | 37 | probes that map specifically to HBA1 or HBA2, potentially indicating a gene conversion
probes that map to both HBA1 and HBA2

At block 504, a quality check may be performed by the decision tree matrix to confirm that the raw data is valid for genotyping analysis. The quality check of the raw data may include the decision tree matrix confirming quality of the raw data using one or more parameters listed in Table 1. In some instances, one or more of the following quality checks are performed and the quality of the raw data is assessed based on the result(s) of the one or more quality checks: (i) a total probe number being equal to a predetermined number of total probes such as 45, (ii) a test (normal) probe number being equal to a predetermined number of test probes such as 33, (iii) a control probe number being equal to a predetermined number of control probes such as 11, (iv) peak signals being greater than or equal to a predetermined peak height threshold (e.g., greater than or equal to 200 RFU after normalization), (v) the Q-fragments (single oligonucleotides (not ligated probes) that will preferentially amplify when the DNA amount is too low or ligation fails) represent ≤a predetermined threshold, e.g., 33% of signal for 92 nt benchmark fragment, (vi) the D-fragments (single oligonucleotides (not ligated probes) that will preferentially amplify when the denaturation reaction is incomplete) represent ≤a predetermined threshold, e.g., 50% of signal for 92 nt benchmark fragment, and (vii) any deviations in the control probe standard deviation greater than a predetermined threshold (e.g., 0.125 threshold). When the quality of the raw data fails, the process stops at block 506, and optionally a request is issued to perform the HBA assay again to obtain new raw data. When the quality of the raw data, the process continues at block 508.

At block 508, a classification of the sample being normal or having a CNV is determined based on sample probe/reference probe ratios indicative of an aberrant probe ratio pattern associated with a CNV. The determination of the classification may comprise identifying, by the decision tree matrix, one or more regions of copy number losses or gains (e.g., deletions, duplications, or point mutations) associated with a CNV based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for all probes listed in Table. 3, (ii) the copy number calling threshold is ≥0.75 and ≤1.3 for predicting the sample as normal, and (iii) the copy number calling threshold is <0.75 or ≥1.3 for predicting the sample as having a CNV. If a result of the analysis is the sample is predicted as being normal, then the sample is classified as normal. If a result of the analysis is the sample is predicted as having a CNV, then the sample is classified as having a CNV. When the sample is classified as normal, the process continues at block 510. When the sample is classified as having a CNV, the process continues at block 512.

At block 510, for any sample having a "normal" or "polymorphism" classification check 13<0.85, 14<0.85, 17<0.85. If true, then aberrant probes are detected and the sample is re-classified as being H aberrant, where H=3. This is essentially a check on repeated probes 13, 14, 17 to determine whether repeated probes 13, 14, 17 are lower than expected. This could indicate a deletion not detected by probes 11, 21, or 22 due to subpar performance. If any of the probes have a probe ratio >0.85, the sample is classified as normal. When the sample is classified as normal or classified as H=3 as the genotype, the process continues at block 540.

At block 512, a classification of the sample having a large deletion is determined based on sample probe/reference probe ratios indicative of an aberrant probe ratio pattern associated with a large deletion. A large deletion encompasses both the HBA1 and HBA2 genes, whereas a small deletion contains only HBA1 or HBA2. The determination of the classification may comprise identifying, by the decision tree matrix, one or more regions of copy number losses or gains (e.g., deletions, duplications, or point mutations) associated with a large deletion based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a first set of probes including probes 8, 10, 11, 13, 14, and 17 listed in Table. 3, (ii) the copy number calling threshold for probe 10 is <0.75 for predicting the sample as having a large deletion, and (iii) the copy number calling threshold for probes 8 and 11 is <0.75 and for probes 13, 14, and 17 is <0.63 for predicting the sample as having a large deletion. If a result of the analysis predicts the sample as having a large deletion, then sample is classified as having a large deletion. If a result of the analysis fails to predict the sample as having a large deletion, then the sample is classified as having a CNV without a large deletion. When the sample is classified as having a large deletion, the process continues at block 528. When the sample is classified as having a CNV without a large deletion, the process continues at block 516.

At block 516, a classification of the sample having a polymorphism is determined based on sample probe/reference probe ratios indicative of an aberrant probe ratio pattern associated with a polymorphism. The determination of the classification may comprise identifying, by the decision tree matrix, one or more regions of copy number losses or gains (e.g., deletions, duplications, or point mutations) associated with a polymorphism based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a second set of probes including probes 4, 8, 11, 21, and 22 listed in Table. 3, and (ii) the copy number calling threshold for probes 4, 8, 11, 21, and 22 is ≥0.75 and ≤1.3. for predicting the sample as being polymorphic. If a result of the analysis predicts the sample as having a polymorphism, then sample is classified as having a polymorphism. If a result of the analysis fails to predict the sample as having a polymorphism, then the sample is classified as having a CNV without a polymorphism. When the sample is classified as being polymorphic, the process continues at block 540. When the sample is classified as having a CNV without polymorphism, the process continues at block 520.

At block 520, a classification of the sample having a $\alpha^{3.7}$ deletion and zygosity is determined based on sample probe/reference probe ratios indicative of an aberrant probe ratio pattern associated with a $\alpha^{3.7}$ deletion and zygosity. The determination of the classification may comprise identifying, by the decision tree matrix, one or more regions of copy number losses or gains (e.g., deletions, duplications, or point mutations) associated with a $\alpha^{3.7}$ deletion and zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a third set of probes including probes 21, 22, and 8 listed in Table. 3 for $\alpha^{3.7}$ homozygous, (ii) the copy number calling threshold checks if 21<0.1, 22<0.1, 8>0.75 for predicting the sample as having a $\alpha^7$ homozygous deletion, (iii) the relative probe ratio data for a fourth set of probes including probes 21, 22, and 8 listed in Table. 3 for $\alpha^{3.7}$ heterozygous, and (iv) the copy number calling threshold checks if 21<0.75, 22<0.75, 8>0.75 for predicting the sample as having a $\alpha^{3.7}$ heterozygous deletion. If a result of the analysis predicts the sample as having a $\alpha^{3.7}$ homozygous deletion, then the sample is classified as having a $\alpha^{3.7}$ homozygous deletion. If a result of the analysis predicts the sample as having a $\alpha^{3.7}$ heterozygous deletion, then the sample is classified as having a $\alpha^7$ heterozygous deletion.

Additionally at block 520, in conjunction with, prior to, or subsequent to determining a classification of the sample having a $\alpha^{3.7}$ deletion and zygosity, a classification of the sample having a $\alpha^{4.2}$ deletion and zygosity is determined based on sample probe/reference probe ratios indicative of an aberrant probe ratio pattern associated with a $\alpha^{4.2}$ deletion and zygosity. The determination of the classification may comprise identifying, by the decision tree matrix, one or more regions of copy number losses or gains (e.g., deletions, duplications, or point mutations) associated with a $\alpha^{3.7}$ deletion and zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a fourth set of probes including probes 11, 21, and 22 listed in Table. 3 for $\alpha^{4.2}$ heterozygous and homozygous, (ii) the copy number calling threshold checks if 11<0.1, 21>0.75, 22>0.75 for predicting the sample as having a $\alpha^{4.2}$ homozygous deletion, and (iii) the copy number calling threshold checks if 11<0.75, 21>0.75, 22>0.75 for predicting the sample as having a $\alpha^{4.2}$ heterozygous deletion. If a result of the analysis predicts the sample as having a $\alpha^{4.2}$ homozygous deletion, then the sample is classified as having a $\alpha^{4.2}$ homozygous deletion. If a result of the analysis predicts the sample as having a $\alpha^{4.2}$ heterozygous deletion, then the sample is classified as having a $\alpha^{4.2}$ heterozygous deletion. If a result of the analysis fails to predict the sample as having a $\alpha^{4.2}$ deletion; however, the result of the $\alpha^{3.7}$ deletion analysis concludes the samples does have a $\alpha^{3.7}$ heterozygous or homozygous deletion, then the sample is classified as having a $\alpha^{3.7}$ heterozygous or homozygous deletion. If a result of the analysis fails to predict the sample as having a $\alpha^{4.2}$ deletion or a $\alpha^{3.7}$ deletion, then the sample is classified as having a CNV without a $\alpha^{4.2}$ heterozygous or homozygous deletion or a $\alpha^{3.7}$ heterozygous or homozygous deletion. When the sample is classified as having a $\alpha^{3.7}$ heterozygous or homozygous deletion or $\alpha^{4.2}$ heterozygous or homozygous deletion, the process continues at block 522. When the sample is classified as having a CNV without a $\alpha^{3.7}$ heterozygous or homozygous deletion or $\alpha^{4.2}$ heterozygous or homozygous deletion, the process continues at block 524.

At block 522, a classification of the sample having a $\alpha^{4.2}$ heterozygous or homozygous deletion, and/or having a $\alpha^{3.7}$ duplication is determined based on sample probe/reference probe ratios indicative of an aberrant probe ratio pattern associated with a $\alpha^{3.7}$ duplication. The determination of the classification may comprise identifying, by the decision tree matrix, one or more regions of copy number losses or gains (e.g., deletions, duplications, or point mutations) associated with a $\alpha^{3.7}$ duplication based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a fifth set of probes including probes 8, 11, 21, and 22 listed in Table. 3 for $\alpha^{3.7}$ duplication when a $\alpha^{4.2}$ heterozygous or homozygous deletion is present, and (ii) the copy number calling threshold checks if 8<1.3, >0.75, 11<0.75, 21>1.3, 22>1.3 for predicting the sample as having a $\alpha^{3.7}$ duplication. If a result of the analysis predicts the sample, classified as having a $\alpha^{4.2}$ heterozygous or homozygous deletion, as also having a $\alpha^{3.7}$ duplication, then the sample is classified as having a $\alpha^{4.2}$ heterozygous or homozygous deletion and a $\alpha^{3.7}$ duplication. If a result of the analysis predicts the sample, classified as having a $\alpha^{4.2}$ heterozygous or homozygous deletion, does not have a $\alpha^{3.7}$ duplication, then the sample is left with the classification of having a $\alpha^{4.2}$ heterozygous or homozygous deletion. When the sample is classified as having a $\alpha^{4.2}$ heterozygous or homozygous deletion and a $\alpha^{3.7}$ duplication, the process continues at block 540. When the sample is classified as having a $\alpha^{3.7}$ heterozygous or homozygous deletion or a $\alpha^{4.2}$ heterozygous or homozygous deletion, the process continues at block 540.

At block 524, a classification of the sample having compound heterozygotes including an $\alpha^{3.7}$ deletion and a $\alpha^{4.2}$ deletion is determined based on sample probe/reference probe ratios indicative of an aberrant probe ratio pattern associated with both a $\alpha^{3.7}$ deletion and a $\alpha^{4.2}$ deletion. The determination of the classification may comprise identifying, by the decision tree matrix, one or more regions of copy number losses or gains (e.g., deletions, duplications, or point mutations) associated with a $\alpha^{3.7}$ deletion and zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a sixth set of probes including probes 8, 29, 1111, 21, 22, 16, and 19 listed in Table. 3 for $\alpha^{3.7}$ deletion and a $\alpha^{4.2}$ deletion, and (ii) the copy number calling threshold checks if 8<1.3, >0.75, 29<1.3, >0.75, 11<0.75, 21<0.75, 22<0.75, either 16<0.1, or 19<0.1 for predicting the sample as having compound heterozygotes including an $\alpha^{3.7}$ deletion and a $\alpha^{4.2}$ deletion. If a result of the analysis predicts the sample as having a compound heterozygotes including an $\alpha^{3.7}$ deletion and a $\alpha^{4.2}$ deletion, then the sample is classified as having a compound heterozygotes including an $\alpha^{3.7}$ deletion and a $\alpha^{4.2}$ deletion. When the sample is classified as having a compound heterozygotes including an $\alpha^{3.7}$ deletion and a $\alpha^{4.2}$ deletion, the process continues at block 540.

Additionally at block 524, in conjunction with, prior to, or subsequent to determining a classification of the sample having a compound heterozygotes including an $\alpha^{3.7}$ deletion and a $\alpha^{4.2}$ deletion, a classification of the sample having a duplication is determined based on sample probe/reference probe ratios indicative of an aberrant probe ratio pattern associated with a duplication. The determination of the classification may comprise identifying, by the decision tree matrix, one or more regions of copy number losses or gains (e.g., deletions, duplications, or point mutations) associated with a duplication based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a seventh set of probes including probes 8, 21, and 22 listed in Table. 3 for duplication, and (ii) the copy number calling threshold checks if 8>0.75, 21>1.3, 22>1.3 for predicting the sample as having a duplication. If a result of the analysis predicts the sample as having a duplication, then the sample is classified as having a duplication. When the sample is classified as having a duplication, the process continues at block 540. If a result of the analysis fails to predict the sample as having a compound heterozygotes including an $\alpha^{3.7}$ deletion and a $\alpha^{4.2}$ deletion and/or a duplication, then the sample is classified as having a CNV without a $\alpha^{4.2}$ heterozygous or homozygous deletion, a $\alpha^{3.7}$ heterozygous or homozygous deletion, and/or a duplication. When the sample is classified as having a CNV without a $\alpha^{4.2}$ heterozygous or homozygous deletion, a $\alpha^{3.7}$ heterozygous or homozygous deletion, and a duplication, the process continues at block 526.

At block 526, a classification of the sample being a CNV that is H aberrant is determined based on sample probe/reference probe ratios indicative of an aberrant probe ratio pattern associated with a CNV that is H aberrant. The determination of the classification may comprise identifying, by the decision tree matrix, one or more regions of copy number losses or gains (e.g., deletions, duplications, or point mutations) associated with a CNV that is H aberrant based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for an eighth set of probes including probes 1, 4-6, 8, 11, 21, 22, 29-37 listed in Table. 3 for a CNV that is H aberrant, and (ii) the copy number calling threshold checks if 8<0.75 or >1.3 for probes 1, 4-6, 8, 11, 21, 22, 29-37 (determines how many important deletion probes are aberrant, and provides a count H of the those probes that are aberrant) for predicting the sample as having a CNV that is H aberrant. If a result of the analysis predicts the sample as having a CNV that is H aberrant, then the sample is classified as a CNV that is H aberrant (where H represents how many important deletion probes are aberrant). When the sample is classified as having a CNV that is H aberrant, the process continues at block 540.

At block 528, a classification of the sample having a large homozygous deletion or a large heterozygous deletion is determined based on sample probe/reference probe ratios indicative of an aberrant probe ratio pattern associated with large deletion zygosity. The determination of the classification may comprise identifying, by the decision tree matrix, one or more regions of copy number losses or gains (e.g., deletions, duplications, or point mutations) associated with large deletion zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a ninth set of probes including probes 8, 10, 13, 14, and 17 listed in Table. 3 for large homozygous deletion, (ii) the copy number calling threshold checks if probes 8, 10, or 13, 14, 17 are <0.1 for predicting the sample as having a large homozygous deletion, (iii) the relative probe ratio data for a tenth set of probes including probes 8, 11, 13, 14, and 17 listed in Table. 3 for large heterozygous deletion, and (iv) the copy number calling threshold checks if probes 8 and 11 <0.75 or 13, 14, 17<0.63 for predicting the sample as having a large heterozygous deletion. If a result of the analysis predicts the sample as having a large homozygous deletion, then the sample is classified as having a large homozygous deletion. If a result of the analysis predicts the sample as having a large heterozygous deletion, then the sample is classified as having a large heterozygous deletion. When the sample is classified as having a large homozygous deletion, the process continues at block 530. When the sample is classified as having a large heterozygous deletion, the process continues at block 532.

At block 530, a classification of the sample having a specific large homozygous deletion is determined based on sample probe/reference probe ratios indicative of an aberrant probe ratio pattern associated with specification deletions including SEA, MED1, MED2, THAI, FIL, and $\alpha^{20.5}$. The determination of the classification may comprise identifying, by the decision tree matrix, one or more regions of copy number losses or gains (e.g., deletions, duplications, or point mutations) associated with a specification deletion based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a eleventh set of probes including probes 8, 31, 32, 5, 6, 33, and 34 listed in Table. 3 for large SEA homozygous deletion, (ii) the copy number calling threshold checks if 8<0.1, 31<0.1, 32<0.1, 5>0.75, 6>0.75, 33>0.75, 34>0.75 for predicting the sample as having a large SEA homozygous deletion, (iii) the relative probe ratio data for a twelfth set of probes including probes 8, 30, 31, 5, 6, 32, and 33 listed in Table. 3 for large MED1 homozygous deletion, (iv) the copy number calling threshold checks if 8<0.1, 30<0.1, 31<0.1, 5>0.75, 6>0.75, 32>0.75, 33>0.75 for predicting the sample as having a large MED1 homozygous deletion, (v) the relative probe ratio data for a thirteenth set of probes including probes 5, 6, 30, 4, 31, and 32 listed in Table. 3 for large MED2 homozygous deletion, (vi) the copy number calling threshold checks if 5<0.1, 6<0.1, 30<0.1, 4>0.75, 31>0.75, 32>0.75 for predicting the sample as having a large MED2 homozygous deletion, (vii) the relative probe ratio data for a fourteenth set of probes including probes 8, 6, 29, and 30 listed in Table. 3 for large $\alpha^{20.5}$ homozygous deletion, (viii) the copy number calling threshold checks if 8<0.1, 6>0.75, 29>0.75, 30>0.75 for predicting the sample as having a large $\alpha^{20.5}$ homozygous deletion, (ix) the relative probe ratio data for a fifteenth set of probes including probes 6, 8, 31, 32, 5, 33, and 34 listed in Table. 3 for large FIL/THAI homozygous deletion, (x) the copy number calling threshold checks if 6<0.1, 8<0.1, 31<0.1, 32<0.1, 5>0.75, 33>0.75, 34>0.75 for predicting the sample as having a large FIL/THAI homozygous deletion, (xi) the relative probe ratio data for a sixteenth set of probes including probes 9, 22, 6, 8, 29, and 30 listed in Table. 3 for large $\alpha^{3.74}/\alpha^{4.2C}$ homozygous deletion, (xii) the copy number calling threshold checks if 9<0.1, 22<0.1, 6>0.75, 8>0.75, 29>0.75, 30>0.75 for predicting the sample as having a large $\alpha^{3.74}/\alpha^{4.2C}$ homozygous deletion, (xiii) the relative probe ratio data for a seventeenth set of probes including probes 11, 21, and 22 listed in Table. 3 for $\alpha^{4.2}$ homozygous deletion, (xiv) the copy number calling threshold checks if 11<0.1, 21>0.75, 22>0.75 for predicting the sample as having a $\alpha^{4.2}$ homozygous deletion, (xv) the relative probe ratio data for a eighteenth set of probes including probes 8, 21, 22, and 11 listed in Table. 3 for large $\alpha^{4.2}$ heterozygous deletion, and (xvi) the copy number calling threshold checks if 8<0.75, >0.25, 21<0.75, >0.25, 22<0.75, >0.25, 11<0.1 for predicting the sample as having a large $\alpha^{4.2}$ heterozygous deletion.

If a result of the analysis predicts the sample as having a large SEA homozygous deletion, then the sample is classified as having a large SEA homozygous deletion. If a result of the analysis predicts the sample as having a large MED1 homozygous deletion, then the sample is classified as having a large MED1 homozygous deletion. If a result of the analysis predicts the sample as having a large MED2 homozygous deletion, then the sample is classified as having a large MED2 homozygous deletion. If a result of the analysis predicts the sample as having a large $\alpha^{205}$ homozygous deletion, then the sample is classified as having a large $\alpha^{20.5}$ homozygous deletion. If a result of the analysis predicts the sample as having a large FIL/THAI homozygous deletion, then the sample is classified as having a large FIL/THAI homozygous deletion. If a result of the analysis predicts the sample as having a large $\alpha^{3.74}\alpha^{4.2C}$ homozygous deletion, then the sample is classified as having a large $\alpha^{3.74}/\alpha^{4.2C}$ homozygous deletion. If a result of the analysis predicts the sample as having a $\alpha^{4.2}$ homozygous deletion, then the sample is classified as having a $\alpha^{4.2}$ homozygous deletion. If a result of the analysis predicts the sample as having a large $\alpha^{4.2}$ heterozygous deletion, then the sample is classified as having a large $\alpha^{4.2}$ heterozygous deletion. When the sample is classified as having a large homozygous deletion, the process continues at block 530. When the sample is classified as having a large SEA, MED1, MED2, $\alpha^{20.5}$, FIL/THAI, or $\alpha^{3.74}/\alpha^{4.2}$c deletion, or $\alpha^{4.2}$ homozygous deletion, or large $\alpha^{4.2}$ heterozygous deletion, the process continues at block 540.

At this point, if the sample remains as a nonspecific classified homozygous deletion (not a large SEA, MED1, MED2, $\alpha^{20.5}$, FIL/THAI, or $\alpha^{3.74}/\alpha^{4.2}$c deletion, or $\alpha^{4.2}$ homozygous deletion, or large $\alpha^{4.2}$ heterozygous deletion), the process continues at block 530 with determining a classification of the sample having a specific large homozygous deletion based on sample probe/reference probe ratios indicative of other aberrant probe ratio patterns associated with specification deletions including $\alpha^{3.7}$, $\alpha^{4.2}$, SEA, MED1, MED2, THAI, FIL, and $\alpha^{20.5}$. The determination of the classification may comprise identifying, by the decision tree matrix, one or more regions of copy number losses or gains (e.g., deletions, duplications, or point mutations) associated with a specification deletion based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a nineteenth set of probes including probes 8, 13, 14, 17, 32, 6, and 33 listed in Table. 3 for large SEA/MED1 homozygous deletion, (ii) the copy number calling threshold checks if 8<0.1, 13<0.1, 14<0.1, 17<0.1, 32<0.75, >0.25, 6>0.75, 33>0.75 for predicting the sample as having a large SEA/MED1 homozygous deletion, (iii) the relative probe ratio data for a twentieth set of probes including probes 8, 13, 14, 17, 30, 31, 5, 6, and 33 listed in Table. 3 for large SEA/(MED2/DUTCH) homozygous deletion, (iv) the copy number calling threshold checks if 8<0.1, 13<0.1, 14<0.1, 17<0.1, 30<0.1, 31<0.75, >0.25, 5<0.75, >0.25, 6>0.75, 33>0.75 for predicting the sample as having a large SEA/(MED2/DUTCH) homozygous deletion, (v) the relative probe ratio data for a twenty-first set of probes including probes 8, 13, 14, 29, 30, 31, 32, 8, and 33 listed in Table. 3 for large SEA/$\alpha^{20.5}$ homozygous deletion, (vi) the copy number calling threshold checks if 8<0.1, 13<0.1, 14<0.1, 29<0.75, >0.25, 30<0.75, >0.25, 31<0.75, >0.25, 32<0.75, >0.25, 6>0.75, 33>0.75 for predicting the sample as having a large SEA/$\alpha^{20.5}$ homozygous deletion, (vii) the relative probe ratio data for a twenty-second set of probes including probes 8, 13, 14, 17, 32, 8, 6, and 33 listed in Table. 3 for large SEA/(FIL/THAI) homozygous deletion, (viii) the copy number calling threshold checks if 8<0.1, 13<0.1, 14<0.1, 17<0.1, 32<0.1, 8<0.75, >0.25, 6>0.75, 33>0.75 for predicting the sample as having a large SEA/(FIL/THAI) homozygous deletion, (ix) the relative probe ratio data for a twenty-third set of probes including probes 8, 13, 14, 17, 30, 31, 5, 6, 4, and 32 listed in Table. 3 for large MED1/(MED2/DUTCH) homozygous deletion, (x) the copy number calling threshold checks if 8<0.1, 13<0.1, 14<0.1, 17<0.1, 30<0.1, 31<0.75, >0.25, 5<0.75, >0.25, 6<0.75, >0.25, 4>0.75, 32>0.75 for predicting the sample as having a large MED1/(MED2/DUTCH) homozygous deletion, (xi) the relative probe ratio data for a twenty-fourth set of probes including probes 8, 13, 14, 17, 31, 6, and 32 listed in Table. 3 for large MED1/$\alpha^{20.5}$ homozygous deletion, (xii) the copy number calling threshold checks if 8<0.1, 13<0.1, 14<0.1, 17<0.1, 31<0.75, >0.25, 6>0.75, 32>0.75 for predicting the sample as having a large MED1/$\alpha^{20.5}$ homozygous deletion, (xiii) the relative probe ratio data for a twenty-fifth set of probes including probes 8, 13, 14, 17, 31, 32, 6, 5, and 33 listed in Table. 3 for large MED1/(FIL/THAI) homozygous deletion, (xiv) the copy number calling threshold checks if 8<0.1, 13<0.1, 14<0.1, 17<0.1, 31<0.1, 32<0.75, >0.25, 6<0.75, >0.25, 5>0.75, 33>0.75 for predicting the sample as having a large MED1/(FIL/THAI) homozygous deletion, (xiii) the relative probe ratio data for a twenty-sixth set of probes including probes 13, 14, 17, 5, 6, 29, 30, 31, and 4 listed in Table. 3 for large (MED2/DUTCH)/$\alpha^{20.5}$ homozygous deletion, (xiv) the copy number calling threshold checks if 13<0.1, 14<0.1, 17<0.1, 5<0.75, >0.25, 6<0.75, >0.25, 29<0.75, >0.25, 30<0.75, >0.25, 31>0.75, 4>0.75 for predicting the sample as having a large (MED2/DUTCH)/$\alpha^{20.5}$ homozygous deletion, (xv) the relative probe ratio data for a twenty-seventh set of probes including probes 8, 13, 14, 17, 6, 31, 5, and 33 listed in Table. 3 for large (MED2/DUTCH)/(FIL/THAI) homozygous deletion, (xvi) the copy number calling threshold checks if 8<0.1, 13<0.1, 14<0.1, 17<0.1, 6<0.75, >0.25, 31<0.75, >0.25, 5>0.75, 33>0.75 for predicting the sample as having a large (MED2/DUTCH)/(FIL/THAI) homozygous deletion, (xvii) the relative probe ratio data for a twenty-eighth set of probes including probes 8, 13, 14, 17, 6, 29, 5, and 33 listed in Table. 3 for large $\alpha^{20.5}$/(FIL/THAI) homozygous deletion, and (xviii) the copy number calling threshold checks if 8<0.1, 13<0.1, 14<0.1, 17<0.1, 6<0.75, >0.25, 29<0.75, >0.25, 5>0.75, 33>0.75 for predicting the sample as having a large $\alpha^{20.5}$/(FIL/THAI) homozygous deletion.

If a result of the analysis predicts the sample as having a large SEA/MED1 homozygous deletion, then the sample is classified as having a large SEA/MED1 homozygous deletion. If a result of the analysis predicts the sample as having a large SEA/(MED2/DUTCH) homozygous deletion, then the sample is classified as having a large SEA/(MED2/DUTCH) homozygous deletion. If a result of the analysis predicts the sample as having a large SEA/(MED2/DUTCH) homozygous deletion, then the sample is classified as having a large SEA/(MED2/DUTCH) homozygous deletion. If a result of the analysis predicts the sample as having a large SEA/$\alpha^{20.5}$ homozygous deletion, then the sample is classified as having a large SEA/$\alpha^{20.5}$ homozygous deletion. If a result of the analysis predicts the sample as having a large SEA/(FIL/THAI) homozygous deletion, then the sample is classified as having a large SEA/(FIL/THAI) homozygous deletion. If a result of the analysis predicts the sample as having a large MED1/(MED2/DUTCH) homozygous deletion, then the sample is classified as having a large MED1/(MED2/DUTCH) homozygous deletion. If a result of the analysis predicts the sample as having a large MED1/$\alpha^{20.5}$ homozygous deletion, then the sample is classified as having a large MED1/$\alpha^{20.5}$ homozygous deletion. If a result of the analysis predicts the sample as having a large MED1/(FIL/THAI) homozygous deletion, then the sample is classified as having a large MED1/(FIL/THAI) homozygous deletion. If a result of the analysis predicts the sample as having a large (MED2/DUTCH)/$\alpha^{20.5}$ homozygous deletion, then the sample is classified as having a large (MED2/DUTCH)/$\alpha^{20.5}$ homozygous deletion. If a result of the analysis predicts the sample as having a large (MED2/DUTCH)/(FIL/THAI) homozygous deletion, then the sample is classified as having a large (MED2/DUTCH)/(FIL/THAI) homozygous deletion. If a result of the analysis predicts the sample as having a large $\alpha^{20.5}$/(FIL/THAI) homozygous deletion, then the sample is classified as having a large $\alpha^{20.5}$/(FIL/THAI) homozygous deletion. At this point, when the sample remains as a nonspecific classified homozygous deletion (not a large SEA, MED1, MED2, $\alpha^{20.5}$, FIL/THAI, or $\alpha^{3.7A}/\alpha^{4.2C}$ deletion, or $\alpha^{4.2}$ homozygous deletion, or large $\alpha^{4.2}$ heterozygous deletion), the process continues at block 540. When the sample is classified as having a large SEA, MED1, MED2, $\alpha^{20.5}$, FIL/THAI, or $\alpha^{3.7A}/\alpha^{4.2C}$ deletion, or $\alpha^{4.2}$ homozygous deletion, or large $\alpha^{4.2}$ heterozygous deletion, the process continues at block 540.

At block 532, a classification of the sample having a specific large heterozygous deletion is determined based on sample probe/reference probe ratios indicative of an aberrant probe ratio pattern associated with specification deletions including SEA, MED1, MED2, THAI, FIL, and $\alpha^{20.5}$. The determination of the classification may comprise identifying, by the decision tree matrix, one or more regions of copy number losses or gains (e.g., deletions, duplications, or point mutations) associated with a specification deletion based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a twenty ninth set of probes including probes 8, 31, 32, 5, 6, 33, and 34 listed in Table. 3 for large SEA heterozygous deletion, (ii) the copy number calling threshold checks if 8<0.75, 31<0.75, 32<0.75, 5>0.75, 6>0.75, 33>0.75, 345>0.75 for predicting the sample as having a large SEA heterozygous deletion, (iii) the relative probe ratio data for a thirtieth set of probes including probes 8, 30, 31, 5, 6, 32, and 33 listed in Table. 3 for large MED1 heterozygous deletion, (iv) the copy number calling threshold checks if 8<0.75, 30<0.75, 31<0.75, 5>0.75, 6>0.75, 32>0.75, 33>0.75 for predicting the sample as having a large MED1 heterozygous deletion, (v) the relative probe ratio data for a thirty-first set of probes including probes 5, 6, 30, 4, 31, and 32 listed in Table. 3 for large MED2 heterozygous deletion, (vi) the copy number calling threshold checks if 5<0.75, 6<0.75, 30<0.75, 4>0.75, 31>0.75, 32>0.75 for predicting the sample as having a large MED2 heterozygous deletion, (vii) the relative probe ratio data for a thirty-second set of probes including probes 8, 6, 29, and 30 listed in Table. 3 for large $\alpha^{20.5}$ heterozygous deletion, (viii) the copy number calling threshold checks if 8<0.75, 6>0.75, 29>0.75, 30>0.75 for predicting the sample as having a large $\alpha^{20.5}$ heterozygous deletion, (ix) the relative probe ratio data for a thirty-third set of probes including probes 6, 8, 31, 32, 5, 33, and 34 listed in Table. 3 for large FIL/THAI heterozygous deletion, (x) the copy number calling threshold checks if 6<0.75, 85<0.75, 31<0.75, 32<0.75, 5>0.75, 33>0.75, 34>0.75 for predicting the sample as having a large FI/THAI heterozygous deletion, (xi) the relative probe ratio data for a thirty-fourth set of probes including probes 9, 22, 6, 8, 29, and 30 listed in Table. 3 for large $\alpha^{3.7A}/\alpha^{4.2C}$ heterozygous deletion, (xii) the copy number calling threshold checks if 9<0.75, 22<0.75, 6>0.75, 8>0.75, 29>0.75, 30>0.75 for predicting the sample as having a large $\alpha^{3.7A}/\alpha^{4.2C}$ heterozygous deletion, (xiii) the relative probe ratio data for a thirty-fifth set of probes including probes 11, 21, and 22 listed in Table. 3 for $\alpha^{4.2}$ homozygous deletion, (xiv) the copy number calling threshold checks if 11<0.1, 21>0.75, 22>0.75 for predicting the sample as having a $\alpha^{4.2}$ homozygous deletion, (xv) the relative probe ratio data for a thirty-sixth set of probes including probes 21, 22, and 11 listed in Table. 3 for large $\alpha^{3.7}$ heterozygous deletion, (xvi) the copy number calling threshold checks if 21<0.15, 22<0.15, 11<0.75, >0.25 for predicting the sample as having a large $\alpha^{3.7}$ heterozygous deletion, (xvii) the relative probe ratio data for a thirty-seventh set of probes including probes 21, 22, and 11 listed in Table. 3 for $\alpha^{3.7}$ homozygous deletion, (xviii) the copy number calling threshold checks if 21<0.15, 22<0.15, 11<0.75, >0.25 for predicting the sample as having a $\alpha^{3.7}$ homozygous deletion, (xix) the relative probe ratio data for a thirty-eighth set of probes including probes 8, 21, 22, and 11 listed in Table. 3 for large $\alpha^{4.2}$ heterozygous deletion, and (xviii) the copy number calling threshold checks if 8<0.75, >0.25, 21<0.75, >0.25, 22<0.75, >0.25, 11<0.1 for predicting the sample as having a large $\alpha^{4.2}$ heterozygous deletion.

If a result of the analysis predicts the sample as having a large SEA heterozygous deletion, then the sample is classified as having a large SEA heterozygous deletion. If a result of the analysis predicts the sample as having a large MED1 heterozygous deletion, then the sample is classified as having a large MED1 heterozygous deletion. If a result of the analysis predicts the sample as having a large MED2 heterozygous deletion, then the sample is classified as having a large MED2 heterozygous deletion. If a result of the analysis predicts the sample as having a large $\alpha^{20.5}$ heterozygous deletion, then the sample is classified as having a large $\alpha^{20.5}$ heterozygous deletion. If a result of the analysis predicts the sample as having a large FIL/THAI heterozygous deletion, then the sample is classified as having a large FIL/THAI heterozygous deletion. If a result of the analysis predicts the sample as having a large $\alpha^{3.7A}/\alpha^{4.2C}$ heterozygous deletion, then the sample is classified as having a large $\alpha^{3.7A}/\alpha^{4.2C}$ heterozygous deletion. If a result of the analysis predicts the sample as having a $\alpha^{4.2}$ homozygous deletion, then the sample is classified as having a $\alpha^{4.2}$ homozygous deletion. If a result of the analysis predicts the sample as having a large $\alpha^{3.7}$ heterozygous deletion, then the sample is classified as having a large $\alpha^{3.7}$ heterozygous deletion. If a result of the analysis predicts the sample as having a $\alpha^{3.7}$ homozygous deletion, then the sample is classified as having a $\alpha^{3.7}$ homozygous deletion. If a result of the analysis predicts the sample as having a large $\alpha^{4.2}$ heterozygous deletion, then the sample is classified as having a large $\alpha^{4.2}$ heterozygous deletion. When the sample is classified as having a large heterozygous deletion, the process continues at block 534. When the sample is classified as having a large SEA, MED1, MED2, $\alpha^{20.5}$, FIL/THAI, or $\alpha^{3.7A}/\alpha^{4.2C}$ or $\alpha^{4.2}$ homozygous deletion, or large $\alpha^{3.7}$ heterozygous deletion, or $\alpha^{3.7}$ homozygous deletion, or large $\alpha^{4.2}$ heterozygous deletion, the process continues at block 536.

At block 534, a classification of the sample having a compound heterozygotic genotype including an unspecified large deletion and a $\alpha^{3.7}$ deletion is determined based on sample probe/reference probe ratios indicative of an aberrant probe ratio pattern associated with both a large deletion and $\alpha^{3.7}$ deletion. The determination of the classification may comprise identifying, by the decision tree matrix, one or more regions of copy number losses or gains (e.g., deletions, duplications, or point mutations) associated with a $\alpha^{3.7}$ deletion and zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a thirty-ninth set of probes including probes 8, 29, 11, 21, 22, 16, and 19 listed in Table. 3 for $\alpha^{3.7}$ deletion, and (ii) the copy number calling threshold checks if 8<0.75, 29<0.75, 11<0.75, 21<0.1, 22<0.1, either 16<0.1, or 19<0.1 for predicting the sample as having compound heterozygotes including an unspecified large deletion and an $\alpha^{3.7}$ deletion. If a result of the analysis predicts the sample as having a compound heterozygotes including a $\alpha^{3.7}$ deletion, then the sample is classified as being a large heterozygous deletion having a compound heterozygotes including an $\alpha^{3.7}$ deletion. If a result of the analysis predicts the sample as not having a compound heterozygotes including a $\alpha^{3.7}$ deletion, then the sample is classified as being a large heterozygous deletion.

Additionally at block 534, a classification of the sample having a compound heterozygotic genotype including an unspecified large deletion and a $\alpha^{4.2}$ deletion is determined based on sample probe/reference probe ratios indicative of an aberrant probe ratio pattern associated with both a large deletion and $\alpha^{4.2}$ deletion. The determination of the classification may comprise identifying, by the decision tree matrix, one or more regions of copy number losses or gains (e.g., deletions, duplications, or point mutations) associated with a $\alpha^{4.2}$ deletion and zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a fortieth set of probes including probes 8, 29, 11, 21, 22, 16, and 19 listed in Table. 3 for $\alpha^{4.2}$ deletion, and (ii) the copy number calling threshold checks if 8<0.75, 29<0.75, 11<0.1, 21<0.75, 22<0.75, for predicting the sample as having compound heterozygotes including an unspecified large deletion and an $\alpha^{4.2}$ deletion. If a result of the analysis predicts the sample as having a compound heterozygotes including a $\alpha^{4.2}$ deletion, then the sample is classified as being a large heterozygous deletion having a compound heterozygotes including an $\alpha^{4.2}$ deletion. If a result of the analysis predicts the sample as not having a compound heterozygotes including a $\alpha^{4.2}$ deletion, then the sample is classified as being a large heterozygous deletion.

Additionally at block 534, in conjunction with, prior to, or subsequent to determining a classification of the sample having a compound heterozygotes including an $\alpha^{3.7}$ deletion and a $\alpha^{4.2}$ deletion, a classification of the sample having a duplication is determined based on sample probe/reference probe ratios indicative of an aberrant probe ratio pattern associated with a duplication. The determination of the classification may comprise identifying, by the decision tree matrix, one or more regions of copy number losses or gains (e.g., deletions, duplications, or point mutations) associated with a duplication based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a forty-first set of probes including probes 8, 21, and 22 listed in Table. 3 for duplication, and (ii) the copy number calling threshold checks if 8<0.75, 21>0.75, 22>0.75 for predicting the sample as having a duplication.

If a result of the analysis predicts the sample, having a unspecified large heterozygous deletion combined with an $\alpha^{3.7}$ deletion or, then the sample is classified as being a large unspecified heterozygous deletion combined with an $\alpha^{3.7}$ deletion. When the sample is classified as being a large unspecified heterozygous deletion having a compound heterozygotes including a $\alpha^{4.2}$ deletion, the process continues at block 540. When the sample is classified as being a large unspecified heterozygous deletion combined with a duplication, the sample is classified as having a large, unspecified deletion and a duplication, and the process continues at block 540. If a result of the analysis predicts the sample, having a large heterozygous deletion, as not having a duplication, then the sample is classified as being a large heterozygous deletion. When the sample is classified as being a large heterozygous deletion, the process continues at block 540.

At block 536, a classification of the sample having compound heterozygotes including an specific targeted large deletion and a $\alpha^{3.7}$ deletion is determined based on sample probe/reference probe ratios indicative of an aberrant probe ratio pattern associated with both a specific targeted large deletion $\alpha^{3.7}$ deletion. The determination of the classification may comprise identifying, by the decision tree matrix, one or more regions of copy number losses or gains (e.g., deletions, duplications, or point mutations) associated with a $\alpha^{3.7}$ deletion and zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a forty-second set of probes including probes 8, 29, 11, 21, 22, 16, and 19 listed in Table. 3 for $\alpha^{3.7}$ deletion, and (ii) the copy number calling threshold checks if 8<0.75, 29<0.75, 11<0.75, 21<0.1, 22<0.1, either 16<0.1, or 19<0.1 for predicting the sample as having compound heterozygotes including a $\alpha^{3.7}$ deletion. If a result of the analysis predicts the sample as having a compound heterozygotes including an $\alpha^{3.7}$ deletion, then the sample is classified as being a specific large heterozygous deletion (e.g., large SEA, MED1, MED2, $\alpha^{20.5}$, FIL/THAI, or $\alpha^{3.74}/\alpha^{4.2C}$) having a compound heterozygotes including an $\alpha^{3.7}$ deletion. If a result of the analysis predicts the sample as not containing a $\alpha^{3.7}$ deletion then the sample is classified as being a specific large heterozygous deletion (e.g., large SEA, MED1, MED2, $\alpha^{20.5}$, FIL/THAI, or $\alpha^{3.74}/\alpha^{4.2C}$.

Additionally at block 536, a classification of the sample having compound heterozygotes including a specific targeted large deletion and a $\alpha^{4.2}$ deletion is determined based on sample probe/reference probe ratios indicative of an aberrant probe ratio pattern associated with both a specific targeted large deletion and a $\alpha^{4.2}$ deletion. The determination of the classification may comprise identifying, by the decision tree matrix, one or more regions of copy number losses or gains (e.g., deletions, duplications, or point mutations) associated with a $\alpha^{4.2}$ deletion and zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a forty-third set of probes including probes 8, 29, 11, 21, 22, 16, and 19 listed in Table. 3 for $\alpha^{3.7}$ deletion, and (ii) the copy number calling threshold checks if 8<0.75, 29<0.75, 11<0.1, 21<0.75, 22<0.75, for predicting the sample as having compound heterozygotes including a $\alpha^{4.2}$ deletion. If a result of the analysis predicts the sample as having a compound heterozygotes including an $\alpha^{4.2}$ deletion, then the sample is classified as being a specific large heterozygous deletion (e.g., large SEA, MED1, MED2, $\alpha^{20.5}$, FIL/THAI, or $\alpha^{3.74}/\alpha^{4.2C}$) having a compound heterozygotes including an $\alpha^{4.2}$ deletion. If a result of the analysis predicts the sample as not containing a $\alpha^{3.7}$ deletion then the sample is classified as being a specific large heterozygous deletion (e.g., large SEA, MED1, MED2, $\alpha^{20.5}$, FIL/THAI, or $\alpha^{3.74}/\alpha^{4.2C}$.

Additionally at block 536, in conjunction with, prior to, or subsequent to determining a classification of the sample having a compound heterozygous deletions including a specific large deletion and a $\alpha^{3.7}$ deletion or a $\alpha^{4.2}$ deletion, a classification of the sample having a specific large deletion and a duplication is determined based on sample probe/reference probe ratios indicative of an aberrant probe ratio pattern associated with a duplication. The determination of the classification may comprise identifying, by the decision tree matrix, one or more regions of copy number losses or gains (e.g., deletions, duplications, or point mutations) associated with a duplication based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a forty-fourth set of probes including probes 8, 21, and 22 listed in Table. 3 for duplication, and (ii) the copy number calling threshold checks if 8>0.1, 21>0.75, 22>0.75 for predicting the sample as having a specific large deletion and a duplication.

If a result of the analysis predicts the sample, having a specific large deletion and a compound heterozygote including a $\alpha^{3.7}$ deletion, then the sample is classified as being a specific large heterozygous deletion having a compound heterozygotes including an $\alpha^{3.7}$ deletion. If a result of the analysis predicts the sample, having a specific large deletion and a compound heterozygote including a duplication, then the sample is classified as being a specific large heterozygous deletion having a compound heterozygotes including a duplication. If a result of the analysis predicts the sample, having a specific large deletion and a compound heterozygote including a $\alpha^{4.2}$ duplication, then the sample is classified as being a specific large heterozygous deletion having a compound heterozygotes including a duplication. When the sample is classified as being a specific large heterozygous deletion having a compound heterozygotes including a $\alpha^{3.7}$ deletion, a $\alpha^{4.2}$ deletion or duplication, the process continues at block 540. If a result of the analysis predicts the sample, having a specific large heterozygous deletion, as not having a $\alpha^{3.7}$ deletion, a $\alpha^{4.2}$ deletion, or a duplication, then the sample is classified as being a specific large heterozygous deletion. When the sample is classified as being a specific large heterozygous deletion, the process continues at block 540.

At block 540, a classification of the sample having a HS40 homozygous deletion or a HS40 heterozygous deletion is determined based on sample probe/reference probe ratios indicative of an aberrant probe ratio pattern associated with HS40 deletion zygosity. The determination of the classification may comprise identifying, by the decision tree matrix, one or more regions of copy number losses or gains (e.g., deletions, duplications, or point mutations) associated with HS40 deletion zygosity based on the new relative probe ratio data and normal ranges (copy number calling thresholds) for the sample probe/reference probe ratios associated with one or more probes. In certain instances, the sample probe/reference probe ratios and copy number calling thresholds used for the analysis include: (i) the relative probe ratio data for a forty-fifth set of probes including probes 1, 4, 2, and 3 listed in Table. 3 for HS40 homozygous deletion, (ii) the copy number calling threshold checks if 1>0.75, <1.3, 4>0.75, <1.3, 2<0.1, 3<0.1 for predicting the sample as having a HS40 homozygous deletion, (iii) the relative probe ratio data for a forty-fifth set of probes including probes 1, 4, 2, and 3 listed in Table. 3 for HS40 heterozygous deletion, and (iv) the copy number calling threshold checks if probes 8 and 1>0.75, <1.3, 4>0.75, <1.3, 2<0.75, 3<0.75 for predicting the sample as having a large heterozygous deletion. Additionally, in instances in which the sample is classified as having a CNV that is H aberrant, the sample probe/reference probe ratios and copy number calling thresholds used for the analysis include: (i) the relative probe ratio data for a forty-second set of probes including probes 2 and 3 listed in Table. 3 for additional aberrant probes, (ii) the copy number calling threshold checks if 2>0.75, 3<0.75 or 2>0.75, 3<0.75 for predicting the sample as having an additional aberrant probe and the number H of probes that are aberrant is updated (if either is true, add 1 to any number H (1-17)).

Additionally at block 540, for any sample having a "normal" or "polymorphism" classification check 13<0.85, 14<0.85, 17<0.85. If true, then aberrant probes are detected and the sample is re-classified as being H aberrant, where H=3. For any sample having a "CNV that is H aberrant" classification, the algorithm checks whether probes 13<0.85, 14<0.85, 17<0.85. If true, then additional aberrant probes are detected and the number H of probes that are aberrant is updated (add 3 to any number H (1-17)).

Additionally at block 540, all samples are checked for a classification of the sample having the Hb Constant Spring single nucleotide variant (SNV). The presence or absence of the SNV is determined by the presence or absence of the Constant Spring SNV probe. In certain instances, the sample probe/reference probe ratios and copy number calling thresholds used for the analysis include: (i) the positive probe signal data for probe 18 listed in Table. 3 for HS40 homozygous deletion, (ii) the probe signal is >0.

If the result of the analysis predicts the sample as having a HS40 homozygous deletion, then prior classification of the sample is concatenated with HS40 homozygous deletion. If the result of the analysis predicts the sample as having a HS40 heterozygous deletion, then prior classification of the sample is concatenated with HS40 heterozygous deletion. If a result of the analysis predicts the sample as not having a HS40 homozygous or heterozygous deletion, then the previous classification of the sample is unchanged. If a result of the analysis predicts the sample as having an additional aberrant probe, then the number H of probes that are aberrant is updated and the classification remains as a CNV that is H aberrant. If the result of the analysis predicts the sample as having a Hb Constant Spring mutation, then prior classification of the sample is concatenated with Hb Constant Spring. If a result of the analysis predicts the sample as not having a Hb Constant Spring, then the previous classification of the sample is unchanged.

The results of this step 540 are a final classification. At this point all samples should be classified as normal, contain only polymorphisms, have one or more confirmable mutations (e.g., $\alpha^{3.7}$, $\alpha^{4.2}$, SEA, MED1, MED2, THAI, FIL, and/or $\alpha^{20.5}$), a CNV with H aberrant probes, or an unclassifiable large deletion. If the sample has a CNV with H aberrant probes or an unclassifiable large deletion the sample should be manually reviewed.

At block 545, the HBA genotype for each sample is determined based on the final classification for each sample. For example, a sample that has a HET $\alpha^{3.7}$ or $\alpha^{4.2}$ deletion AND HET SEA, FIL, MED, THAI, or $\alpha^{20.5}$ classification would be genotyped as --/-α (see, e.g., Table 2). At optional block 550, a risk score(s) may be computed based on the HBA genotype and result implication determined for each sample, as shown in Table 2. In some instances, the risk score(s) may identify: (i) a risk of the subject being a carrier of the $\alpha^{3.7}$, $\alpha^{4.2}$, SEA, MED, THAI, FIL, $\alpha^{20.5}$ and HS-40 deletions and Hb Constant Spring point mutation, (ii) a risk for couples identified as being a carrier of the $\alpha^{3.7}$, $\alpha^{4.2}$, SEA, MED, THAI, FIL, $\alpha^{20.5}$ and HS-40 deletions and Hb Constant Spring point mutation, and/or (iii) a risk of a fetus inheriting the $\alpha^{3.7}$, $\alpha^{4.2}$, SEA, MED, THAI, FIL, $\alpha^{20.5}$ and HS-40 deletions and Hb Constant Spring point mutation.

At block 555, the HBA genotype determined for each allele and optional risk score(s) may be output. The output of the HBA genotype determined for each allele and optional risk score(s) may comprise providing an end user with the output and/or recording the output in a storage device (e.g., displaying the output on a user interface and/or storing the output in a results file of a database).

Figure 6:
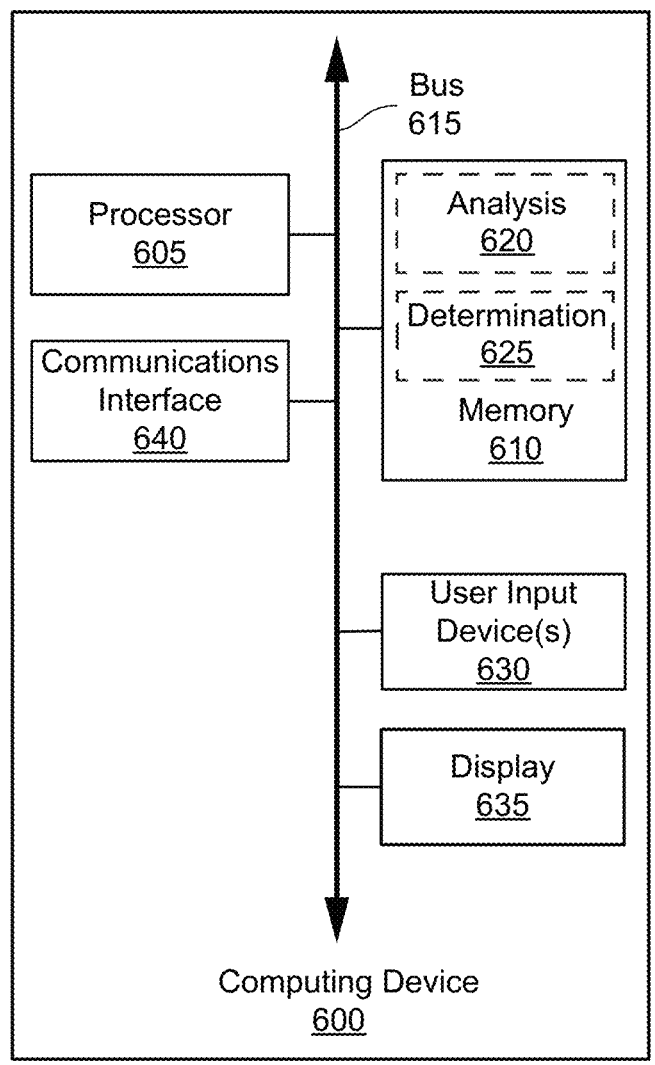
FIG. 6 shows an exemplary computing device in accordance with various embodiments.

FIG. 6 illustrates an example computing device 600 suitable for use with systems and methods for HBA genotyping using a HBA assay platform and genotyping techniques according to this disclosure. The example computing device 600 includes a processor 605 which is in communication with the memory 610 and other components of the computing device 600 using one or more communications buses 615. The processor 605 is configured to execute processor-executable instructions stored in the memory 610 to perform one or more methods for searching and identifying HBA peaks that are present within the raw data, determining an HBA genotype of a specimen, and/or determining a risk score of a patient according to different examples, such as part or all of the example process 400 or 500 described above with respect to FIGS. 4 and 5. In this example, the memory 610 stores processor-executable instructions that provide HBA peak analysis 620 and HBA genotype determination 625, as discussed above with respect to FIGS. 1, 2, 4, and 5.

The computing device 600, in this example, also includes one or more user input devices 630, such as a keyboard, mouse, touchscreen, microphone, etc., to accept user input. The computing device 600 also includes a display 635 to provide visual output to a user such as a user interface. The computing device 600 also includes a communications interface 640. In some examples, the communications interface 640 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

IV. EXAMPLES

The systems and methods implemented in various embodiments may be better understood by referring to the following examples.

Example 1: The HBA Assay and the HBA Genotyping Decision Tree Matrix

Specimens, Data Collection, and HBA Assay Analysis

Genomic DNA was extracted from 224 bloods, 41 prenatal specimens and 2 cell lines (Coriell NA03433, NA10797) were used in this exemplary study. Of the blood specimens, 49 were either fresh or archived specimens. Prior to de-identification, any α-thalassemia genotype information, if available, was retained for each sample. All specimens were anonymized prior to their use in this exemplary study. Raw data were collected on an ABI 3730XL genetic analyzer using the ABI Foundation Data Collection software v3.0 and uploaded into a GeneMarker software v2.7.0 for analysis of sample quality, generation of the synthetic reference and normalization of sample signal to that of the synthetic reference to detect deletions and duplications. The quality metrics for analysis are listed in Table 1. The manufacturer's recommended thresholds for relative probe ratios (fold changes v. reference) when no deletions or duplications are present were used in this study. The threshold for the control probe standard deviation was determined empirically.

Analytical Sensitivity and Specificity

To establish analytical sensitivity and specificity, 69 specimens and cell lines of known genotypes (39 positives and 30 negatives; Table 4) were tested in the HBA MLPA assay as described with respect to FIGS. 1-3. Genotype calls were made with both the HBA Genotyping decision tree matrix (discussed with respect to FIGS. 4 and 5) and by manual review. All samples were quantified using a SpectraMax M2 Fluorometer, and inputs ranged from 12.5 ng to 100 ng. The genotypes were blinded to the operator prior to their use.

TABLE 4

List of Deletion and Duplication Genotypes

| Genotype | Number of Samples |
|---|---|
| $\alpha^{3.7}$ deletion, HET | 6 |
| $\alpha^{3.7}$ deletion, HOM | 8 |
| $\alpha^{4.2}$ deletion, HET | 1 |
| $\alpha^{3.7}$ deletion/$\alpha^{4.2}$ deletion, cpd HET | 2 |
| $\alpha^{20.5}$ deletion, HET | 1 |
| SEA deletion, HET | 4 |
| SEA deletion/$\alpha^{3.7}$ deletion, cpd HET | 1 |
| SEA deletion/FIL deletion, cpd HET | 1 |
| FIL deletion, HET | 2 |
| MED deletion, HET | 1 |
| THAI deletion, HET | 1 |
| HS40 deletion, HET | 1 |
| BRIT deletion, HET | 2 |
| $\alpha^{3.7}$ duplication, HET | 4 |
| $\alpha^{4.2}$ duplication, HET | 1 |
| --/-$\alpha$ | 1 |
| --/-- | 2 |
| Normal and Polymorphisms | 30 |

Quality Metrics

The overall average control probe standard deviation was 0.048±0.030. Of the 69 samples tested, six did not initially pass the sample quality metrics (6/69; 8.7%; Table 5) and were repeated with the same aliquots of DNA. The inputs for three of these samples were 15 ng, 16 ng and 29 ng, which are below the lower limit that is recommended by the manufacturer (50-100 ng). The other three samples had been archived frozen for at least 15 years, and no information on the extraction method used was available. Upon retesting, all 6 samples passed quality metrics and were deemed acceptable for genotype calling (Table 5).

TABLE 5

Quality Metrics for Sensitivity/Specificity Sample Set

| Number of Samples | Average of Control probe std dev | Std dev of control probe std dev | No. of samples failing QC-$1^{st}$ pass | No. of samples failing QC $2^{nd}$ pass |
|---|---|---|---|---|
| Positive: 39 | 0.052 | 0.031 | 3 | 0 |
| Negative: 30 | 0.043 | 0.028 | 3 | 0 |
| Total: 69 | 0.048 | 0.030 | 6 | 0 |

Genotype Calls

All samples were analyzed using the quality check thresholds in Table 1. With either the HBA genotyping decision tree matrix (discussed with respect to FIGS. 4 and 5) or by manual analysis, no false negatives were detected, and all 30 negative samples were called correctly, resulting in 100% specificity. Of the 39 positive samples, 35 and 37 samples were called for a targeted genotype with the HBA genotyping decision tree matrix and by manual analysis, respectively (Table 6). For the samples in which the variations were detected but the genotypes not specifically called, two were duplications and were not targeted variants.

For the two duplication samples, manual analysis correctly identified one as a heterozygous $\alpha^{3.7}$ duplication (sample ZZ-59) and the other as a heterozygous $\alpha^{442}$ duplication (sample ZZ-48). The HBA genotyping decision tree matrix also detected the duplications but could not assign one of the targeted genotypes to them and instead, flagged these samples for manual review. That is, for ZZ-59, all but one probe for the $\alpha^{3.7}$ region was above the 1.30 threshold to call the duplication and rather than call this as a normal, the HBA genotyping decision tree matrix flagged it for manual review. As for ZZ-48 with the $\alpha^{442}$ duplication, the HBA genotyping decision tree matrix was not programmed to call this particular genotype. Importantly, for either sample, the HBA genotyping decision tree matrix did not miss the call but rather defaulted to manual review.

Although not one of the intended targeted mutations for this assay, two samples that were heterozygous for a BRIT deletion were included in this study to test the HBA genotyping decision tree matrix. With both the HBA genotyping decision tree matrix and by manual analysis, the samples were called as heterozygous SEA deletions since the same MLPA probes will detect either a SEA or BRIT deletion. Multiplex PCR did not confirm the SEA deletion in either sample. The SEA deletion call by HBA MLPA for these samples should not be considered false positive since the BRIT deletion is not a targeted mutation in the assay and both calling methods did detect a large deletion that was about the same size as the BRIT deletion. Since the HBA MLPA assay can detect any number of large deletions besides those targeted for this test that could have clinical significance, the HBA genotyping decision tree matrix was designed to ensure that any copy number changes detected by multiple probes were not missed and instead went to manual review. Thus, all targeted mutations were identified in the positive samples, resulting in an assay sensitivity of 100% using either the HBA genotyping decision tree matrix or manual method.

TABLE 6

Summary of Sensitivity/Specificity Genotype Calls

| | | Decision Tree Matrix | | | Manual | |
|---|---|---|---|---|---|---|
| Sample | Number of Samples | Correct Genotype Call | Call after Manual Review | CNV Detected and Correct Genotype CNV Detected | Correct Genotype Call | CNV Detected |
| Positive | 39 | 35 | 2 | 2* | 37 | 2* |
| Negative | 30 | 30 | 0 | 0 | 30 | 0 |

*BRIT Deletions

Reproducibility

Figure 7:
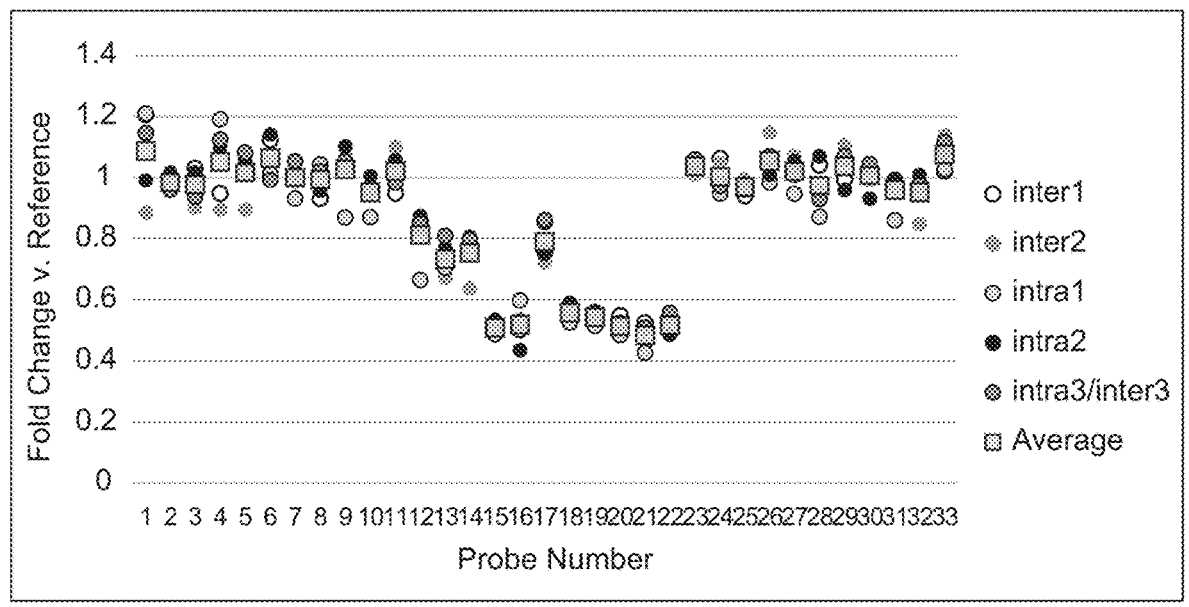
FIG. 7 shows a probe-by-probe plot of fold change relative to reference for an $\alpha^{3.7}$ HET deletion (sample B09) in accordance with various embodiments.

For intra-assay reproducibility, 3 samples were tested in triplicate on the same assay run. These same samples were also used for inter-assay reproducibility with a second lot of reagents, different operator and on different days. Data analysis was carried out by both a manual analysis and the HBA genotyping decision tree matrix. For both intra-assay and inter-assay reproducibility, all but one sample (G05-intra1) passed QC metrics for control probe standard deviation (Table 7) although replicates of this sample passed suggesting that sample quality was not the issue. The MLPA Lane Score or quality control fragments did not detect issues with the MLPA reaction and no evaporation was visibly detected for this sample. With passing samples, the fold change v. reference for each probe was reproducible (see, FIG. 7 for example—Single probes (#15,16,19-23) consistently detected the deletion at ~0.5 fold change and with duplicated probes (#13,14,17) at ~0.75. Polymorphic probe #12 also detected a deletion at ~0.75 fold change, indicating the likely span of this particular $\alpha^{3.7}$ deletion), and genotype calls with the algorithm were 100% concordant with the calls made manually. Based on this data, the assay was reproducible from run to run.

TABLE 7

Intra- and Inter- Assay Reproducibility Results

| | QC Metrics | Decision Tree Matrix | | |
| --- | --- | --- | --- | --- |
| Sample | Metrics Control Probe | Number of Control Probes | Number* of Normal Probes | Number* of Del/Dup Probes | Matrix/ Manual Call |
| B09-intra 1 | 0.097 | 11 | 23 | 10 | $\alpha^{3.7}$ het |
| B09-intra2 | 0.06 | 11 | 23 | 10 | $\alpha^{3.7}$ het |
| B09-intra3/ inter3 | 0.071 | 11 | 23 | 10 | $\alpha^{3.7}$ het |
| B09-inter1 | 0.049 | 11 | 23 | 10 | $\alpha^{3.7}$ het |
| B09-inter2 | 0.064 | 11 | 23 | 10 | $\alpha^{3.7}$ het |
| C01-intra1 | 0.029 | 11 | 33 | 0 | Normal |
| C01-intra2 | 0.068 | 11 | 33 | 0 | Normal |
| C01-intra3/ inter3 | 0.07 | 11 | 33 | 0 | Normal |

TABLE 7-continued

Intra- and Inter- Assay Reproducibility Results

| | QC Metrics | Decision Tree Matrix | | |
| --- | --- | --- | --- | --- |
| Sample | Metrics Control Probe | Number of Control Probes | Number* of Normal Probes | Number* of Del/Dup Probes | Matrix/ Manual Call |
| C01-inter1 | 0.043 | 11 | 33 | 0 | Normal |
| C01-inter2 | 0.066 | 11 | 33 | 0 | Normal |
| G05-intra1 | 0.147 | 11 | 27 | 6 | Fail |
| G05-intra2 | 0.055 | 11 | 28 | 5 | Polymorphism |
| G05-intra3/ inter3 | 0.093 | 11 | 27 | 6 | Polymorphism |
| G05-inter1 | 0.043 | 11 | 27 | 6 | Polymorphism |
| G05-inter2 | 0.094 | 11 | 27 | 6 | polymorphism |

*Total Normal Probe Number = number of normal probes + number of del/dup probes

HBA Genotyping Decision Tree Matrix Performance

The performance of the HBA genotyping decision tree matrix was further evaluated with 267 blinded specimens. Genotype calls were compared to that by manual review and/or results from previous testing by another laboratory. Overall, the HBA genotyping decision tree matrix and manual method/previous testing results agreed for 261 samples (261/267; 97.8%; Table 8) at first pass through the HBA MLPA assay. Two samples with minimal genotyping information, one labeled as 'hydrops' and the other as 'Hemo. H', were genotyped by the HBA genotyping decision tree matrix as a homozygous SEA deletion and a SEA deletion in trans with $\alpha^{3.7}$ deletion, respectively, and confirmed by multiplex PCR. In addition, as aforementioned, two samples with BRIT deletions that are indistinguishable from the SEA deletions by the HBA MLPA assay were not confirmed as SEA or any of the other targeted deletions in the multiplex PCR assay. These samples would be repeated in the MLPA assay for confirmation testing in the clinical laboratory.

TABLE 8

Performance of Genotyping Algorithm Compared to Manual Analysis

| Sample No. | Sample Genotype | Truth | Correct Genotype Called | | Incorrect Genotype Called | |
| --- | --- | --- | --- | --- | --- | --- |
| | | | Matrix | Manual | Matrix | Manual |
| 1 | Normal | 164 | 161* | 164 | 0 | 0 |
| 2 | Polymorphism | 28 | 28 | 28 | 0 | 0 |
| 3 | HS40 del | 1 | 1 | 1 | 0 | 0 |
| 4 | $\alpha^{3.7}$ or $\alpha^{4.2}$ deletion | 35 | 35 | 35 | 0 | 0 |
| 6 | SEA, FIL, THAI, MED, $\alpha^{20.5}$ deletion | 9 | 9 | 9 | 2** | 2** |
| 7 | combination of 4 & 6 in trans | 19 | 19 | 19 | 0 | 0 |
| 8 | $\alpha^{3.7}$ duplication | 7 | 6* | 7 | 0 | 0 |
| 9 | $\alpha^{4.2}$ duplication | 2 | 0* | 2 | 0 | 0 |
| | Total: | 267 | 265 | 265 | 2 | 2 |

*Samples that were not specifically called for expected genotype by the HBA genotyping decision tree matrix but instead indicated for Director review
**Two samples with BRIT deletions that are indistinguishable from the SEA deletions by the HBA MLPA assay The HIBA genotyping decision tree matrix is trained to detect fold change patterns in normalized sample probes whether or not it can assign one of the targeted genotypes, and as shown in Table 9, all six samples that the algorithm marked for clinical director review were due to inconsistencies in the configuration of the relative probe ratios for a region. In addition, the HIBA genotyping decision tree matrix is designed to error on the side of sensitivity (i.e., false positives) rather than miss any calls (i.e., false negatives). Thus, although the HBA genotyping decision tree matrix did not specifically call the $\alpha^{3.7}$ duplication, it did detect an anomaly with one probe and rather than miss the call, flagged the sample for manual review. Likewise, with the three normal samples, the HBA genotyping decision tree matrix identified irregularities with the relative probe ratio for multiple probes and designated these for manual review instead of miscalling the genotypes.

TABLE 9

Discrepancy in Calls Between the Genotyping Algorithm and Manual Method

| Truth | Number of Samples | Matrix Call | Reason for Discrepancy |
| --- | --- | --- | --- |
| $\alpha^{3.7}$ dup | 1 | Manual Review | One probe slightly below 1.30 fold change dup calling threshold; probe pattern recognized as abnormal -> marked for review |
| $\alpha^{4.2}$ dup | 2 | Manual Review | $\alpha^{4.2}$ genotype is not included in the algorithm; probe pattern recognized as abnormal -> marked for review |
| Normal | 3 | Manual Review | Multiple specific probes slightly above/below normal calling thresholds; probe pattern recognized as abnormal-designated for review |

Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:
   obtaining nucleic acid from a plurality of samples;
   performing a Hemoglobin A (HBA) assay on the nucleic acid to obtain raw data, wherein the HBA assay is performed using a plurality of probes capable of detection of copy number losses or gains in an α-globin gene cluster region of each sample of the plurality of samples, and the raw data comprises HBA copy number data for the plurality of probes;
   selecting, by a computing system, a reference sample from the plurality of samples, wherein the reference sample is selected based on variability among the plurality of probes and a determination of an absence of a copy number variation based on the raw data for the plurality of probes for the reference sample;

calculating, by the computing system, a first set of probe ratios for each sample of the plurality of samples based on the raw data from the HBA assay and the reference sample;

identifying, by the computing system, a predetermined number of reference samples to be combined as a synthetic reference sample for the plurality of samples based on the first set of probe ratios;

generating, by the computing system, a list of the predetermined number of reference samples;

generating, by the computing system, the synthetic reference sample as a concatenation of the predetermined number of reference samples in the list;

calculating, by the computing system, a second set of probe ratios for each sample of the plurality of samples based on the raw data from the HBA assay and the synthetic reference sample;

iteratively inputting, by the computing system, the second set of probe ratios for each sample into a decision tree matrix;

determining, by the computing system using the decision tree matrix, an HBA genotype for each sample based on the second set of probe ratios for each sample and copy number calling thresholds for sample probe/reference probe ratios associated with each probe of the plurality of probes;

determining, by the computing system, one or more particular copy number variations are assigned to one or more samples of the plurality of samples based on the HBA genotype determined for each of the one or more samples; and performing a confirmation test by multiplex assay methodology and gel electrophoresis or Sanger sequencing for a subset of samples, wherein each sample in the subset of samples is determined to have the one or more particular copy number variations.

2. The computer-implemented method of claim 1, wherein the calculating the first set of probe ratios comprises: (i) comparing control probe peak heights, or signals, in each sample of the plurality of samples to corresponding control probe peak heights, or signals, in the reference sample, (ii) calculating variability in signals between the control probe peak heights, or signals, in each sample and the corresponding control probe peak heights, or signals, in the reference sample as a control probe standard deviation, (iii) determining a sample of the plurality of samples fails when any variability metrics are greater than a predetermined threshold, (iv) determining a sample of the plurality of samples does not fail when none of the variability metrics are greater than the predetermined threshold, and (v) for each sample that does not fail, comparing test probe peak heights, or signals, in the sample to corresponding test probe peak heights in the reference sample, and calculating a probe ratio between the test probe peak heights, or signals, in the sample and the corresponding test probe peak heights, or signals, in the reference sample.

3. The computer-implemented method of claim 2, wherein the calculating the second set of probe ratios comprises: (i) comparing the control probe peak heights, or signals, in each sample of the plurality of samples to corresponding control probe peak heights, or signals, in the synthetic reference sample, (ii) calculating variability in signals between the control probe peak heights, or signals, in each sample and the corresponding control probe peak heights, or signals in the synthetic reference sample as a control probe standard deviation, (iii) determining a sample of the plurality of samples fails when any variability metrics are greater than the predetermined threshold, (iv) determining a sample of the plurality of samples does not fail when none of the variability metrics are greater than the predetermined threshold, and (v) for each sample that does not fail, comparing test probe peak heights, or signals, in the sample to corresponding test probe peak heights in the synthetic reference sample, and calculating a probe ratio between the test probe peak heights, or signals, in the sample and the corresponding test probe peak heights, or signals, in the synthetic reference sample.

4. The computer-implemented method of claim 3, wherein the determining the HBA genotype for each sample comprises: (i) determining aberrant probe ratio patterns for each sample based on the second set of probe ratios for each sample and the copy number calling thresholds for the sample probe/reference probe ratios associated with each probe of the plurality of probes, and (ii) identify the HBA genotype for each sample based on the aberrant probe ratio patterns.

5. The computer-implemented method of claim 4, wherein the determining the aberrant probe ratio patterns and the identifying the HBA genotype for each sample comprises:

classifying each sample as normal, having a copy number variation (CNV), or as polymorphic based on the aberrant probe ratio patterns; and sub classifying any sample classified as having the CNV as a large targeted deletion, duplication or 'other' based on the aberrant probe ratio patterns.

6. The computer-implemented method of claim 5, wherein the determining the aberrant probe ratio patterns and the identifying the HBA genotype for each sample further comprises:

sub classifying any sample classified as having the large targeted deletion as a large heterozygous deletion or a homozygous deletion;

sub classifying any sample classified as the large heterozygous deletion or the homozygous deletion for one or more of the following deletions: SEA, FIL/THAI, MED or $\alpha^{20.5}$ based on the aberrant probe ratio patterns;

sub classifying any sample classified as having the large heterozygous deletion for one or more of the following: $\alpha^{3.7}$ deletions, $\alpha^{4.2}$ deletions and/or $\alpha^{3.7}$ duplications based on the aberrant probe ratio patterns; or sub classifying any sample classified as 'other' as having $\alpha^{3.7}$ deletions, $\alpha^{4.2}$ deletions, and/or $\alpha^{3.7}$ duplications based on the aberrant probe ratio patterns.

7. The computer-implemented method of claim 1, wherein the performing the HBA assay comprises:

obtaining a pool of oligonucleotides, wherein the pool of oligonucleotides targets regions comprising an α-globin gene cluster region;

hybridizing the nucleic acid with the pool of oligonucleotides or a derivative thereof to obtain a plurality of probes for each sample of the plurality of samples; and resolving the plurality of probes for each sample of the plurality of samples by capillary electrophoresis to obtain raw data, wherein the raw data comprises HBA copy number data for the plurality of probes.

8. The computer-implemented method of claim 7, wherein the performing the HBA assay further comprises:

hybridizing a primer of each oligonucleotide of the pool of oligonucleotides to the nucleic acid from the plurality of samples;
ligating the hybridized oligonucleotides to the nucleic acid to obtain the plurality of probes; and
amplifying the ligated probes to obtain the raw data.

\* \* \* \* \*